United States Patent
Ebeling et al.

(10) Patent No.: US 9,956,223 B2
(45) Date of Patent: May 1, 2018

(54) SCREENING METHOD

(71) Applicant: Hoffmann-La Roche Inc., Little Falls, NJ (US)

(72) Inventors: Martin Ebeling, Grenzach-Wyhlen (DE); Friedrich Metzger, Freiburg (DE); Manaswini Sivaramakrishnan, Basel (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days. days.

(21) Appl. No.: 15/048,653

(22) Filed: Feb. 19, 2016

(65) Prior Publication Data

US 2017/0241983 A1    Aug. 24, 2017
US 2018/0024115 A9    Jan. 25, 2018

Related U.S. Application Data

(63) Continuation of application No. PCT/EP2014/067476, filed on Aug. 15, 2014.

(30) Foreign Application Priority Data

Aug. 19, 2013 (EP) .................... 13180825

(51) Int. Cl.
*A61K 31/519* (2006.01)
*C12Q 1/68* (2018.01)
*G01N 33/50* (2006.01)

(52) U.S. Cl.
CPC .......... *A61K 31/519* (2013.01); *C12Q 1/6886* (2013.01); *G01N 33/5011* (2013.01); *C12Q 2600/136* (2013.01); *C12Q 2600/156* (2013.01); *G01N 2333/4706* (2013.01); *G01N 2500/10* (2013.01)

(58) Field of Classification Search
CPC ................................................. A61K 31/519
See application file for complete search history.

(56) References Cited

U.S. PATENT DOCUMENTS

| | | | |
|---|---|---|---|
| 8,633,019 B2 | 1/2014 | Paushkin et al. | |
| 9,371,336 B2 | 6/2016 | Lee et al. | |
| 9,399,649 B2 | 7/2016 | Chen et al. | |
| 9,586,955 B2 | 3/2017 | Qi et al. | |
| 9,617,268 B2 | 4/2017 | Woll et al. | |
| 2014/0135705 A1 | 5/2014 | Hourmand et al. | |
| 2015/0080383 A1 | 3/2015 | Yang et al. | |
| 2016/0145270 A1 | 5/2016 | Dakka et al. | |
| 2017/0001995 A1 | 1/2017 | Metzger et al. | |
| 2017/0129885 A1 | 5/2017 | Qi et al. | |
| 2017/0197969 A1 | 7/2017 | Pinard et al. | |
| 2017/0197990 A1 | 7/2017 | Ratni et al. | |

FOREIGN PATENT DOCUMENTS

| | | | | |
|---|---|---|---|---|
| WO | 1998/39332 A1 | 9/1998 | | |
| WO | 2009/151546 A2 | 12/2009 | | |
| WO | 2010/083338 A2 | 7/2010 | | |
| WO | 2013/101974 A1 | 7/2013 | | |
| WO | 2013/112788 A1 | 8/2013 | | |
| WO | 2013/119916 A2 | 8/2013 | | |
| WO | 2013/130689 A1 | 9/2013 | | |
| WO | 2013/142236 A1 | 9/2013 | | |
| WO | 2014/209841 A2 | 12/2014 | | |
| WO | 2015/024876 A3 | 2/2015 | | |
| WO | WO 2015/024876 | * | 2/2015 | ........... A61K 31/519 |
| WO | 2015/173181 A1 | 11/2015 | | |
| WO | 2015/197503 A1 | 12/2015 | | |
| WO | 2016/128343 A1 | 8/2016 | | |
| WO | 2016/184832 A1 | 11/2016 | | |

OTHER PUBLICATIONS

Wang et al., "Forkhead box M1 transcription factor: A novel target for cancer therapy" Cancer Treatment Reviews 36:151-156 (2010).
International Preliminary Report on Patentability issued in International Application No. PCT/EP2014/067476, dated Feb. 23, 2016, in 11 pages.
EP Communication dated Feb. 19, 2018.For EP Application No. 14 750 760.2.
Visnyei et al., "A molecular screening approach to identify and characterize inhibitors of glioblastoma stem cells" Molecular Cancer Therapeutics 10(10):1818-1828 (Aug. 22, 2011).

* cited by examiner

*Primary Examiner* — Erich A Leeser

(74) *Attorney, Agent, or Firm* — Zong-Qiang Bill Tian

(57) ABSTRACT

The invention discloses a screening method for the identification of new compounds for use in the treatment of cancer.

9 Claims, 8 Drawing Sheets

SCREENING METHOD

RELATED APPLICATIONS

This application is a continuation of International Application No. PCT/EP2014/067476, filed Aug. 15, 2014, which claims the benefit of priority under 35 USC 119(a) to European patent application number EP13180825.5, filed Aug. 19, 2013, the disclosure of each of which is incorporated herein by reference in its entirety.

SEQUENCE LISTING

The instant application contains a Sequence Listing which has been submitted in ASCII format via EFS-Web and is hereby incorporated by reference in its entirety. Said ASCII copy, created on Feb. 18, 2016, is named P31257-US and is 79,177 bytes in size.

FIELD OF THE INVENTION

The present invention relates to a screening method for the identification of compounds useful in the treatment of cancer and compounds identified by the method of the invention.

BACKGROUND

FoxM1 is a transcription factor of the Forkhead family. It is also known in the literature as Trident (in mouse), HFH-11 (in human), WIN or INS-1 (in rat), MPP-2 (partial human cDNA) or FKHL-16. The Forkhead family comprises a large number of transcription factors defined by a conserved DNA binding domain called Forkhead or winged-helix domain. The FoxM1 gene was cloned by screening cDNA libraries with degenerate primers for homologues with a conserved Forkhead DNAbinding domain (W. Korver, J. Roose, H. Clevers, Nucleic Acids Res. 25 (1997) 1715-1719). The FoxM1 gene was revealed to encode a Forkhead transcription factor family member that exhibits 45% identity in the DNA-binding domain with five of its closest related Forkhead members, namely FoxA3 (HNF-3γ, FoxC1 (fkh-1), FoxF2 (FREAC-2), FoxK1 (ILF) and FoxN2 (HTLF). The FoxM1 C-terminal region was found to have homology (76% identity) with a human partial cDNA encoding an open reading-frame of 221 amino acids, termed MPP-2. MPP-2 stands for MPM-2-reactive phosphoprotein-2 and was identified after screening a lymphoblast-derived cDNA library with the MPM-2 monoclonal antibody, which binds specifically to epitopes on mitotic proteins that are phosphorylated in a phosphoserine-proline dependent manner. FoxM1 binds DNA in vitro through the consensus site TAAACA. This motif shares the core sequence recognized by other members of the forkhead family. In particular, repeats of these motifs, in alternating orientation, were often characterized within the selected binding sequences for FoxM1.

The human FoxM1 gene is a 10-exon structure spanning approximately 25 kb on the 12p13-3 chromosomal band (telomeric position) (W. Korver, J. Roose, H. Clevers, Nucleic Acids Res. 25 (1997) 1715-1719). Two exons, named exons Va and VIIa, also referred to as exon A1 (or rat exon 6) and A2 respectively, are alternatively spliced (H. Ye, T. F. Kelly, U. Samadani, L. Lim, S. Rubio, D. G. Overdier, K. A. Roebuck, R. H. Costa, Mol. Cell Biol. 17 (1997) 1626-1641). Exon Va encodes a 15 amino-acid insertion within the C-terminal part of the DNA binding-domain, and is not seen in any of the other Forkhead transcription factor family members. Exon VIIa represents a 38 amino-acid insertion within the C-terminus of the protein. Differential splicing of exons Va and VIIa in human FoxM1, gives rise to three classes of transcripts, class A containing both alternative exons, class B containing none of the alternative exons, and class C in which exon Va only is retained (H. Ye, T. F. Kelly, U. Samadani, L. Lim, S. Rubio, D. G. Overdier, K. A. Roebuck, R. H. Costa, Mol. Cell Biol. 17 (1997) 1626-1641). Both FoxM1B and FoxM1C are transcriptionally active, whereas FoxM1A is transcriptionally inactive, due to the insertion of exon VIIa in the C-terminal transactivation domain. This disruption of the transactivation domain in FoxM1A not only leads to transcriptional inactivation, it might also cause this variant to act as a dominant-negative variant as it has retained normal DNA binding activity in the absence of a functional transactivation domain (H. Ye, T. F. Kelly, U. Samadani, L. Lim, S. Rubio, D. G. Overdier, K. A. Roebuck, R. H. Costa, Mol. Cell Biol. 17 (1997) 1626-1641).

FoxM1 is overexpressed in a broad range of tumor types, including those of neural, gastrointestinal, and reproductive origin (see Bektas et al., supra; Nakamura et al., 2004, Oncogene 23: 2385-400; Pilarsky et al., 2004, Neoplasia. Q: 744-50; Liu et al., 2006, Cancer Res 66: 3593-602). This expression pattern of FoxM1 is attributed to the ability of FoxM1 to transactivate genes required for cell cycle progression (Wang et al., 2002, Proc Nat. Acad Sci USA 99:16881-6). Increased nuclear staining of FoxM1B found in human basal cell carcinomas suggests that FoxM1 is required for cellular proliferation in human cancers (Teh et al., 2002, Cancer Res. 62: 4773-80). The detailed role of FoxM1 in establishing or facilitating tumor progression and disease management has not been fully elucidated, however.

EP 2 298 896 discloses siRNA molecules inhibiting expression of FoxM1B protein and the use of the siRNA molecules for inhibiting tumor growth.

WO 2011/127297 discloses a composition comprising a FoxM1 inhibitor and Herceptin for the treatment of breast cancer. The inhibitor is for example a FoxM1 specific siRNA or a thiazole antibiotic such as thiostrepton.

The problem to be solved by the present invention was to provide new compounds for the treatment of cancer.

SUMMARY

In a first aspect the present invention provides compounds inducing alternative splicing of the FoxM1 gene (splicing modifiers) for use in the prophylaxis or treatment of cancer, wherein the compound induces a transcriptionally inactive FoxM1 variant.

In a particular embodiment, the transcriptionally inactive FoxM1 variant is FoxM1A.

In a particular embodiment, the FoxM1 gene is the human FoxM1 gene.

In a particular embodiment, the cancer is selected from the group consisting of cancer of the liver, prostate, brain, breast, lung, colon, pancreas, skin, cervix, ovary, mouth, blood and nervous system.

In a particular embodiment, the FoxM1 splicing modifier for use in the prophylaxis or treatment of cancer is a compound of formula I:

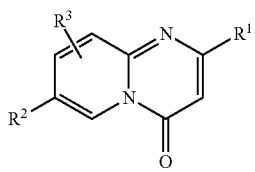

(I)

wherein $R^1$ is selected from aryl, heteroaryl, heterocycloalkyl, which all three substituents are optionally substituted by $C_{1-7}$ alkyl, $C_{1-7}$ alkoxy, $C_{1-7}$ haloalkoxy, $C_{1-7}$haloalkyl, halogen, hydroxyl, cyano, $NO_2$;

$R^2$ is $C_{1-7}$ alkoxy optionally substituted by heterocycloalkyl, NR'R", or heterocycloalkyl optionally substituted by hydroxy, NR'R"—$C_{1-7}$ alkyl, hydroxy-$C_{1-7}$ alkyl, $C_{3-8}$ cyclopropyl, heterocycloalkyl, $C_{1-7}$ alkoxy-$C_{1-7}$ alkyl, hydroxy-$C_{1-7}$ alkoxy-$C_{1-7}$ alkyl, halogen or azaspirocycloalkyl, azabicyloalkyl, $C_{2-7}$ alkynyl optionally substituted by NR'R", or heteroaryl optionally substituted by $C_{1-7}$ alkyl, $R^3$ is halogen, $C_{1-7}$ alkyl, R' and R" are independently selected from hydrogen, $C_{1-7}$ alkyl, hydroxy-$C_{1-7}$ alkyl.

In a particular embodiment, the FoxM1 splicing modifier for use in the prophylaxis or treatment of cancer is a compound of formula (I), wherein $R^1$ is aryl or heteroaryl both substituents optionally substituted by $C_{1-7}$ alkyl, $C_{1-7}$ haloalkyl, halogen, $C_{1-7}$ alkoxy, NR'R", $R^2$ is heteroaryl or heterocycloalkyl both substituents optionally substituted by $C_{1-7}$ alkyl, hydroxy-$C_{1-7}$ alkyl, halo-$C_{1-7}$ alkyl, $R^3$ is $C_{1-7}$ alkyl.

In a particular embodiment the invention relates to compounds of formula (I), wherein:

$R^1$ is phenyl, imidazo[1,2-a]pyrazinyl, pyrazolo[1,5-a]pyrazinyl, imidazo[1,2-a]pyridinyl, 1,3-benzoxazolyl, indazolyl.

In a particular embodiment, the FoxM1 splicing modifier for use in the prophylaxis or treatment of cancer is a compound of formula (I), wherein $R^2$ is piperidinyl, morpholinyl, piperazinyl, pyridinyl, 1,2,3,6-tetrahydropyridinyl, pyrrolidinyl.

The present invention further provides the use of a compound of the present invention for the preparation of a medicament for the prophylaxis or treatment or of cancer.

In a further aspect the present invention provides a pharmaceutical formulation comprising a compound of the present invention.

In a further aspect the present invention provides a method for the prophylaxis or treatment of cancer comprising administering an effective amount of a compound of the present invention to a subject in need thereof.

In a further aspect the present invention provides a method of screening for compounds for the prophylaxis or treatment of cancer comprising:
a) contacting proliferating cells expressing the FoxM1 gene with a test compound,
b) measuring the FoxM1 variant FoxM1A in the cells of step a), wherein an increased level of the FoxM1A variant compared to a control is indicative for a compound for the prophylaxis or treatment of cancer.

In a further aspect the present invention provides a method of screening for compounds for the prophylaxis or treatment of cancer comprising:
a) contacting proliferating cells expressing the FoxM1 gene with a test compound,
b) measuring the FoxM1 variant FoxM1B and/or variant FoxM1C in the cells of step a), wherein a decreased level of the variant FoxM1B and/or variant FoxM1C compared to a control is indicative for a compound for the prophylaxis or treatment of cancer.

In a particular embodiment of the method of the present invention the cells are fibroblasts.

In a particular embodiment of the method of the present invention the FoxM1 variants are measured on RNA level.

In a particular embodiment of the method of the present invention the FoxM1 variants are measured on protein level.

BRIEF DESCRIPTION OF THE FIGURES

FIG. 1A., upregulation of FoxM1A mRNA; FIG. 1B., downregulation of FoxM1B/C mRNA; FIG. 1C., Correlation of EC50 values for FoxM1A upregulation and FoxM1B/C downregulation. Data represent means±SEM of 4 independent observations.

FIG. 2A., Micronuclei induction (MNT) in fibroblasts with increasing doses of cpd. 1-4; FIG. 2B., Dose-dependent induction of cytotoxicity by cpds. 1-4. expressed as % of untreated control after 24 hours. A cut-off at 75% (ED75%, dashed line) defined the concentration at which a meaningful impact on proliferation and cell survival was observed. FIG. 2C., Dose-dependent reduction of Cell Index by cpds. 1-4. expressed as % of untreated control. A cut-off at 75% (EC75%, dashed line) defined the concentration at which a meaningful impact on proliferation and cell survival was observed. Data represent means±SEM of 4 independent observations.

FIG. 3A., Correlation of micronucleus induction (2%, M) with EC50 (FoxM1ΔA2); FIG. 3B., Correlation of cytotoxicity (ED75%) with EC50 (FoxM1ΔA2). FIG. 3C., Correlation of Cell Index (EC75%) with EC50 (FoxM1 ΔA2). Data represent means±SEM of 4 independent observations.

FIG. 4A., Correlation of micronucleus induction (2%, M) with EC50 (FoxM1 FL); FIG. 4B., Correlation of cytotoxicity (ED75%) with EC50 (FoxM1 FL). FIG. 4C., Correlation of Cell Index (EC75%) with EC50 (FoxM1 FL). Data represent means±SEM of 4 independent observations.

FIG. 5A., FoxM1A and actin Western blots from samples treated without (control) or with cpd. 3 (0.1, 1 and 10 µM); FIG. 5B., Protein levels of actin (surrogate for cell number); FIG. 5C., FoxM1A/actin ratio. Data represent means±SEM of 3 independent observations. Statistical comparison was performed by one-way ANOVA followed by Dunnet's post-hoc test. *, $p<0.05$, , $p<0.01$, *, $p<0.001$.

FIG. 6A., FoxM1A and actin Western blots from samples treated without (control) or with cpd. 3 (0.1, 1 and 10 µM). Note that FoxM1A protein was undetectable; FIG. 6B., Protein levels of actin. Data represent means±SEM of 3 independent observations. Statistical comparison was performed by one-way ANOVA followed by Dunnet's post-hoc test.

DETAILED DESCRIPTION OF EMBODIMENTS OF THE INVENTION

Figure 1A:
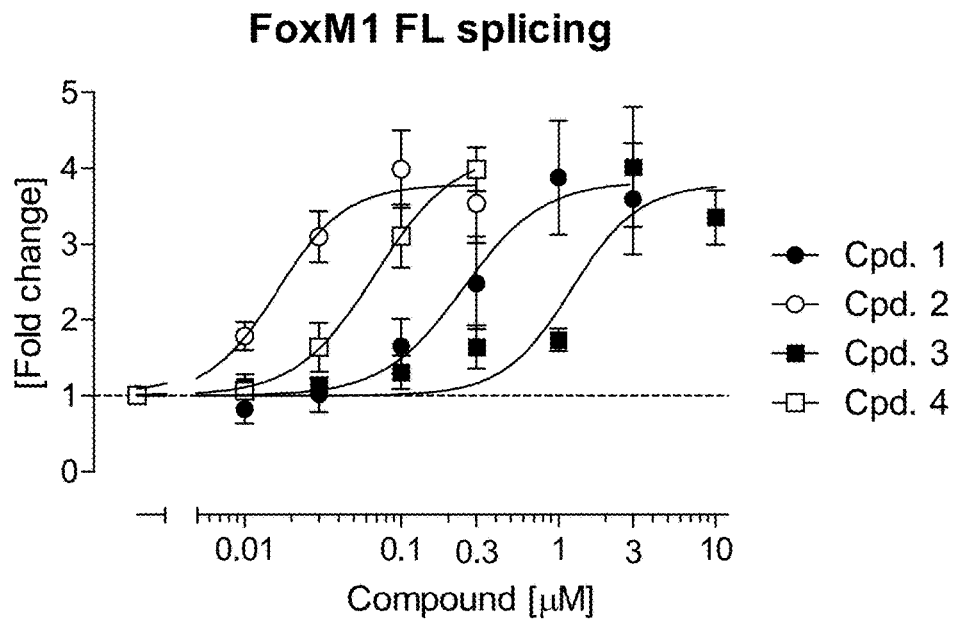
FIGS. 1A, 1B and 1C. Induction of alternative splicing of FoxM1 towards FoxM1A in fibroblasts. Human fibroblasts were incubated with cpds. 1-4 at different doses for 24 hours, and changes in FoxM1A RNA (containing exon A2) and FoxM1B/C (lacking exon A2) mRNA expression were assessed by RT-qPCR. Dose response curves were fitted to a Hill binding equation to estimate the EC50.
Figure 1B:
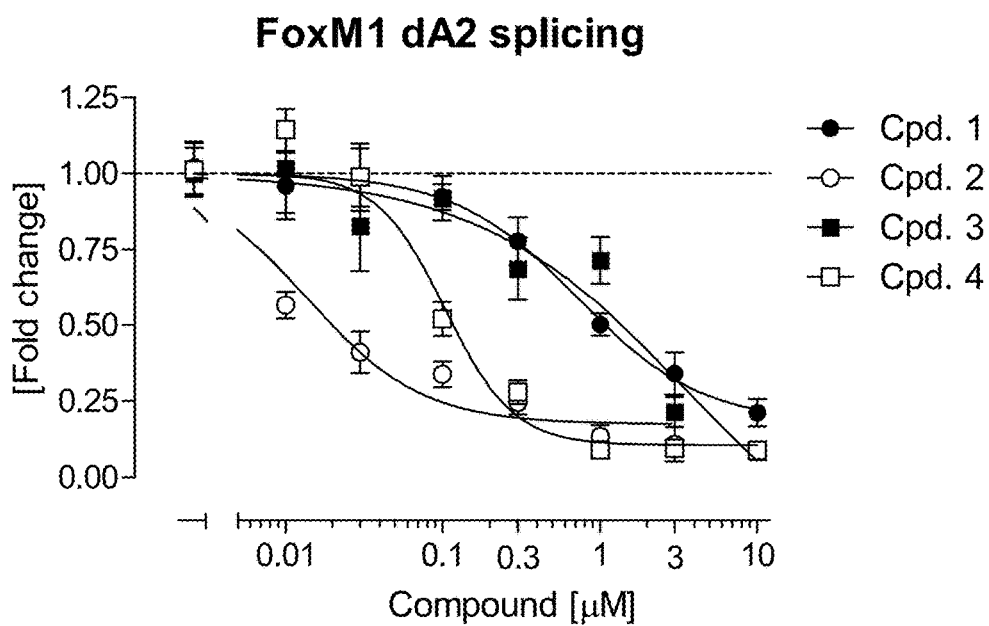

The term "FoxM1 polypeptide" is used herein to refer to native FoxM1 polypeptide from any animal, e.g. mammalian, species, including humans, and FoxM1 variants. The amino acid sequence of human FoxM1A polypeptide is given in Seq. Id. No. 1, the amino acid sequence of human FoxM1B is given in Seq. Id. No. 2 and the amino acid sequence of FoxM1C polypeptide is given in Seq. Id. No. 3.

The nucleotide sequences of the three FoxM1 variants are set forth in Seq. Id. No. 4 (FoxM1A), Seq. Id. No. 5 (FoxM1B) and Seq. Id. No. 6 (FoxM1C).

The term "compound modifying splicing of the FoxM1 gene" is used herein to refer to compounds which lead to the production of transcriptionally inactive forms of the FoxM1 polypeptide, in particular to the production of FoxM1A variant, by modifying the FoxM1 splicing such that transcriptionally inactive forms are generated, in particular FoxM1A, and by suppressing the production of transcriptionally active FoxM1 variants, in particular FoxM1B and FoxM1C.

The term "compound" is used herein in the context of a "test compound" or a "drug candidate compound" described in connection with the assays of the present invention. As such, these compounds comprise organic or inorganic compounds, derived synthetically or from natural sources. The compounds include inorganic or organic compounds such as polynucleotides, lipids or hormone analogs that are characterized by relatively low molecular weights. Other biopolymeric organic test compounds include peptides comprising from about 2 to about 40 amino acids and larger polypeptides comprising from about 40 to about 500 amino acids, such as antibodies or antibody conjugates.

Methods for detection and/or measurement of polypeptides in biological material are well known in the art and include, but are not limited to, Western-blotting, Flow cytometry, ELISAs or RIAs, or various proteomics techniques. An example for a method to measure a polypeptide is an ELISA. This type of protein quantitation is based on an antibody capable of capturing a specific antigen, and a second antibody capable of detecting the captured antigen. The assays mentioned hereinbefore are described in Harlow, E. and Lane, D. Antibodies: A Laboratory Manual, (1988), Cold Spring Harbor Laboratory Press.

Methods for detection and/or measurement of RNA in biological material are well known in the art and include, but are not limited to, Northern-blotting, RNA protection assay, RT PCR. Suitable methods are described in Molecular Cloning: A Laboratory Manual (Fourth Edition) By Michael R. Green, Joseph Sambrook, Peter MacCallum © 2012, 2,028 pp, ISBN 978-1-936113-42-2.

The term "compound(s) of this invention" and "compound(s) of the present invention" refers to compound(s) modifying splicing of the FoxM1 gene, in particular to compounds of formula (I), and stereoisomers, tautomers, solvates, and salts (e.g., pharmaceutically acceptable salts) thereof.

The term "pharmaceutically acceptable salts" denotes salts which are not biologically or otherwise undesirable. Pharmaceutically acceptable salts include both acid and base addition salts.

The term "pharmaceutically acceptable acid addition salt" denotes those pharmaceutically acceptable salts formed with inorganic acids such as hydrochloric acid, hydrobromic acid, sulfuric acid, nitric acid, carbonic acid, phosphoric acid, and organic acids selected from aliphatic, cycloaliphatic, aromatic, araliphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, maloneic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid, ethanesulfonic acid, p-toluenesulfonic acid, and salicyclic acid.

The term "pharmaceutically acceptable base addition salt" denotes those pharmaceutically acceptable salts formed with an organic or inorganic base. Examples of acceptable inorganic bases include sodium, potassium, ammonium, calcium, magnesium, iron, zinc, copper, manganese, and aluminum salts. Salts derived from pharmaceutically acceptable organic nontoxic bases includes salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-di ethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperizine, piperidine, N-ethylpiperidine, and polyamine resins.

The term "alkoxy" denotes a group of the formula —O—R', wherein R' is an alkyl group. Examples of alkoxy moieties include methoxy, ethoxy, isopropoxy, and tert-butoxy.

The term "alkoxyalkyl" denotes an alkyl group wherein at least one of the hydrogen atoms of the alkyl group has been replaced by an alkoxy group. Exemplary alkoxyalkyl groups include 2-methoxyethyl, 3-methoxypropyl, 1-methyl-2-methoxyethyl, 1-(2-methoxyethyl)-3-methoxypropyl, and 1-(2-methoxyethyl)-3-methoxypropyl.

The term "alkyl" denotes a monovalent linear or branched saturated hydrocarbon group of 1 to 12 carbon atoms. In particular embodiments, alkyl has 1 to 7 carbon atoms, and in more particular embodiments 1 to 4 carbon atoms. Examples of alkyl include methyl, ethyl, propyl, isopropyl, n-butyl, iso-butyl, sec-butyl, or tert-butyl.

The term "alkynyl" denotes a monovalent linear or branched saturated hydrocarbon group of 2 to 7 carbon atoms comprising one, two or three triple bonds. In particular embodiments alkynyl has from 2 to 4 carbon atoms comprising one or two triple bonds. Examples of alkynyl include ethynyl, propynyl, prop-2-ynyl, isopropynyl, n-butynyl, and iso-butynyl.

The term "aryl" denotes a monovalent aromatic carbocyclic mono- or bicyclic ring system comprising 6 to 10 carbon ring atoms. Examples of aryl moieties include phenyl and naphthyl.

The term "cycloalkyl" denotes a monovalent saturated monocyclic or bicyclic hydrocarbon group of 3 to 10 ring carbon atoms. In particular embodiments cycloalkyl denotes a monovalent saturated monocyclic hydrocarbon group of 3 to 8 ring carbon atoms. Bicyclic means consisting of two saturated carbocycles having one or more carbon atoms in common. Particular cycloalkyl groups are monocyclic. Examples for monocyclic cycloalkyl are cyclopropyl, cyclobutanyl, cyclopentyl, cyclohexyl or cycloheptyl. Examples for bicyclic cycloalkyl are bicyclo[2.2.1]heptanyl, or bicyclo[2.2.2]octanyl.

The term "haloalkoxy" denotes an alkoxy group wherein at least one of the hydrogen atoms of the alkoxy group has been replaced by same or different halogen atoms, particularly fluoro atoms. Examples of haloalkoxyl include monofluoro-, difluoro- or trifluoro-methoxy, -ethoxy or -propoxy, for example 3,3,3-trifluoropropoxy, 2-fluoroethoxy, 2,2,2-trifluoroethoxy, fluoromethoxy, or trifluor-methoxy. The term "perhaloalkoxy" denotes an alkoxy group where all hydrogen atoms of the alkoxy group have been replaced by the same or different halogen atoms.

The term "haloalkyl" denotes an alkyl group wherein at least one of the hydrogen atoms of the alkyl group has been replaced by same or different halogen atoms, particularly fluoro atoms. Examples of haloalkyl include monofluoro-, difluoro- or trifluoro-methyl, -ethyl or -propyl, for example 3,3,3-trifluoropropyl, 2-fluoroethyl, 2,2,2-trifluoroethyl, fluoromethyl, or trifluoromethyl. The term "perhaloalkyl" denotes an alkyl group where all hydrogen atoms of the alkyl group have been replaced by the same or different halogen atoms.

The term "heteroaryl" denotes a monovalent aromatic heterocyclic mono- or bicyclic ring system of 5 to 12 ring atoms, comprising 1, 2, 3 or 4 heteroatoms selected from N, O and S, the remaining ring atoms being carbon. Examples of heteroaryl moieties include pyrazolo[1,5-a]pyrazinyl, pyrrolyl, furanyl, thienyl, imidazolyl, oxazolyl, thiazolyl, triazolyl, oxadiazolyl, thiadiazolyl, tetrazolyl, pyridinyl, pyrazinyl, pyrazolyl, pyridazinyl, pyrimidinyl, triazinyl, azepinyl, diazepinyl, isoxazolyl, benzofuranyl, isothiazolyl, benzothienyl, indolyl, isoindolyl, isobenzofuranyl, benzimidazolyl, benzoxazolyl, benzoisoxazolyl, benzothiazolyl, benzoisothiazolyl, benzooxadiazolyl, benzothiadiazolyl, benzotriazolyl, purinyl, quinolinyl, isoquinolinyl, quinazolinyl, or quinoxalinyl.

The term "heterocycloalkyl" denotes a monovalent saturated or partly unsaturated mono- or bicyclic ring system of 3 to 9 ring atoms, comprising 1, 2, or 3 ring heteroatoms selected from N, O and S, the remaining ring atoms being carbon. In particular embodiments, heterocycloalkyl is a monovalent saturated monocyclic ring system of 4 to 7 ring atoms, comprising 1, 2, or 3 ring heteroatoms selected from N, O and S, the remaining ring atoms being carbon. Examples for monocyclic saturated heterocycloalkyl are aziridinyl, oxiranyl, azetidinyl, oxetanyl, pyrrolidinyl, tetrahydrofuranyl, tetrahydro-thienyl, pyrazolidinyl, imidazolidinyl, oxazolidinyl, isoxazolidinyl, thiazolidinyl, piperidinyl, tetrahydropyranyl, tetrahydrothiopyranyl, piperazinyl, morpholinyl, thiomorpholinyl, 1,1-dioxo-thiomorpholin-4-yl, azepanyl, diazepanyl, homopiperazinyl, or oxazepanyl. Examples for bicyclic saturated heterocycloalkyl are 8-aza-bicyclo[3.2.1]octyl, quinuclidinyl, 8-oxa-3-aza-bicyclo[3.2.1]octyl, 9-aza-bicyclo[3.3.1]nonyl, 3-oxa-9-aza-bicyclo[3.3.1]nonyl, or 3-thia-9-aza-bicyclo[3.3.1]nonyl. Examples for partly unsaturated heterocycloalkyl are dihydrofuryl, imidazolinyl, dihydro-oxazolyl, tetrahydro-pyridinyl, or dihydropyranyl.

The term "hydroxyalkyl" denotes an alkyl group wherein at least one of the hydrogen atoms of the alkyl group has been replaced by a hydroxy group. Examples of hydroxyalky include hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 2-hydroxy-1-hydroxymethylethyl, 2,3-dihydroxybutyl, 3,4-dihydroxybutyl or 2-(hydroxymethyl)-3 hydroxypropyl.

The term "optional" or "optionally" denotes that a subsequently described event or circumstance may but need not occur, and that the description includes instances where the event or circumstance occurs and instances in which it does not.

The term "substituted" denotes that a specified group bears one or more substituents. Where any group may carry multiple substituents and a variety of possible substituents is provided, the substituents are independently selected and need not to be the same. The term "unsubstituted" means that the specified group bears no substituents. The term "optionally substituted" means that the specified group is unsubstituted or substituted by one or more substituents, independently chosen from the group of possible substituents. When indicating the number of substituents, the term "one or more" means from one substituent to the highest possible number of substitution, i.e. replacement of one hydrogen up to replacement of all hydrogens by substituents.

Pharmaceutical Compositions and Administration

Another embodiment provides pharmaceutical compositions or medicaments containing the compounds of the invention and a therapeutically inert carrier, diluent or excipient, as well as methods of using the compounds of the invention to prepare such compositions and medicaments. In one example, compounds of formula I may be formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but preferably ranges anywhere from about 3 to about 8. In one example, a compound of formula I is formulated in an acetate buffer, at pH 5. In another embodiment, the compounds of formula I are sterile. The compound may be stored, for example, as a solid or amorphous composition, as a lyophilized formulation or as an aqueous solution.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "effective amount" of the compound to be administered will be governed by such considerations, and is the minimum amount necessary to modify FoxM1 gene splicing. For example, such amount may be below the amount that is toxic to normal cells, or the mammal as a whole.

The compounds of the invention may be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, or subcutaneous administration.

The compounds of the present invention may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents.

A typical formulation is prepared by mixing a compound of the present invention and a carrier or excipient. Suitable carriers and excipients are well known to those skilled in the art and are described in detail in, e.g., Ansel, Howard C., et al., Ansel's Pharmaceutical Dosage Forms and Drug Delivery Systems. Philadelphia: Lippincott, Williams & Wilkins, 2004; Gennaro, Alfonso R., et al. Remington: The Science and Practice of Pharmacy. Philadelphia: Lippincott, Williams & Wilkins, 2000; and Rowe, Raymond C. Handbook of Pharmaceutical Excipients. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

An example of a suitable oral dosage form is a tablet containing about 25 mg, 50 mg, 100 mg, 250 mg, or 500 mg of the compound of the invention compounded with about 90-30 mg anhydrous lactose, about 5-40 mg sodium croscarmellose, about 5-30 mg polyvinylpyrrolidone (PVP) K30, and about 1-10 mg magnesium stearate. The powdered ingredients are first mixed together and then mixed with a solution of the PVP. The resulting composition can be dried, granulated, mixed with the magnesium stearate and compressed to tablet form using conventional equipment. An example of an aerosol formulation can be prepared by dissolving the compound, for example 5-400 mg, of the invention in a suitable buffer solution, e.g. a phosphate buffer, adding a tonicifier, e.g. a salt such sodium chloride, if desired. The solution may be filtered, e.g., using a 0.2 micron filter, to remove impurities and contaminants.

An embodiment, therefore, includes a pharmaceutical composition comprising a compound of Formula I or a stereoisomer or pharmaceutically acceptable salt thereof. In a further embodiment includes a pharmaceutical composition comprising a compound of Formula I, or a stereoisomer or pharmaceutically acceptable salt thereof, together with a pharmaceutically acceptable carrier or excipient.

Another embodiment includes a pharmaceutical composition comprising a compound of formula I for use in the treatment of a hyperproliferative disease. Another embodiment includes a pharmaceutical composition comprising a compound of Formula I for use in the treatment of cancer.

In specific embodiments, the cancer treated by the compounds of the present invention is leukemia, acute myeloid leukemia, colon cancer, gastric cancer, macular degeneration, acute monocytic leukemia, breast cancer, hepatocellular carcinoma, cone-rod dystrophy, alveolar soft part sarcoma, myeloma, skin melanoma, prostatitis, pancreatitis, pancreatic cancer, retinitis, adenocarcinoma, adenoiditis, adenoid cystic carcinoma, cataract, retinal degeneration, gastrointestinal stromal tumor, Wegener's granulomatosis, sarcoma, myopathy, prostate adenocarcinoma, Hodgkin's lymphoma, ovarian cancer, non-Hodgkin's lymphoma, multiple myeloma, chronic myeloid leukemia, acute lymphoblastic leukemia, renal cell carcinoma, transitional cell carcinoma, colorectal cancer, chronic lymphocytic leukemia, anaplastic large cell lymphoma, kidney cancer, breast cancer, cervical cancer.

In specific embodiments, the cancer prevented and/or treated in accordance with the present invention is basal cell carcinoma, goblet cell metaplasia, or a malignant glioma, cancer of the liver, breast, lung, prostate, cervix, uterus, colon, pancreas, kidney, stomach, bladder, ovary, or brain.

In specific embodiments, the cancer prevented and/or treated in accordance with the present invention include, but are not limited to, cancer of the head, neck, eye, mouth, throat, esophagus, esophagus, chest, bone, lung, kidney, colon, rectum or other gastrointestinal tract organs, stomach, spleen, skeletal muscle, subcutaneous tissue, prostate, breast, ovaries, testicles or other reproductive organs, skin, thyroid, blood, lymph nodes, kidney, liver, pancreas, and brain or central nervous system.

Specific examples of cancers that can be prevented and/or treated in accordance with present invention include, but are not limited to, the following: renal cancer, kidney cancer, glioblastoma multiforme, metastatic breast cancer; breast carcinoma; breast sarcoma; neurofibroma; neurofibromatosis; pediatric tumors; neuroblastoma; malignant melanoma; carcinomas of the epidermis; leukemias such as but not limited to, acute leukemia, acute lymphocytic leukemia, acute myelocytic leukemias such as myeloblastic, promyelocytic, myelomonocytic, monocytic, erythroleukemia leukemias and myclodysplastic syndrome, chronic leukemias such as but not limited to, chronic myelocytic (granulocytic) leukemia, chronic lymphocytic leukemia, hairy cell leukemia; polycythemia vera; lymphomas such as but not limited to Hodgkin's disease, non-Hodgkin's disease; multiple myelomas such as but not limited to smoldering multiple myeloma, nonsecretory myeloma, osteosclerotic myeloma, plasma cell leukemia, solitary plasmacytoma and extramedullary plasmacytoma; Waldenstrom's macroglobulinemia; monoclonal gammopathy of undetermined significance; benign monoclonal gammopathy; heavy chain disease; bone cancer and connective tissue sarcomas such as but not limited to bone sarcoma, myeloma bone disease, multiple myeloma, cholesteatoma-induced bone osteosarcoma, Paget's disease of bone, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, neurilemmoma, rhabdomyosarcoma, and synovial sarcoma; brain tumors such as but not limited to, glioma, astrocytoma, brain stem glioma, ependymoma, oligodendroglioma, nonglial tumor, acoustic neurinoma, craniopharyngioma, medulloblastoma, meningioma, pineocytoma, pineoblastoma, and primary brain lymphoma; breast cancer including but not limited to adenocarcinoma, lobular (small cell) carcinoma, intraductal carcinoma, medullary breast cancer, mucinous breast cancer, tubular breast cancer, papillary breast cancer, Paget's disease (including juvenile Paget's disease) and inflammatory breast cancer; adrenal cancer such as but not limited to pheochromocytom and adrenocortical carcinoma; thyroid cancer such as but not limited to papillary or follicular thyroid cancer, medullary thyroid cancer and anaplastic thyroid cancer; pancreatic cancer such as but not limited to, insulinoma, gastrinoma, glucagonoma, vipoma, somatostatin-secreting tumor, and carcinoid or islet cell tumor; pituitary cancers such as but limited to Cushing's disease, prolactin-secreting tumor, acromegaly, and diabetes insipius; eye cancers such as but not limited to ocular melanoma such as iris melanoma, choroidal melanoma, and cilliary body melanoma, and retinoblastoma; vaginal cancers such as squamous cell carcinoma, adenocarcinoma, and melanoma; vulvar cancer such as squamous cell carcinoma, melanoma, adenocarcinoma, basal cell carcinoma, sarcoma, and Paget's disease; cervical cancers such as but not limited to, squamous cell carcinoma, and adenocarcinoma; uterine cancers such as but not limited to endometrial carcinoma and uterine sarcoma; ovarian cancers such as but not limited to, ovarian epithelial carcinoma, borderline tumor, germ cell tumor, and stromal tumor; cervical carcinoma; esophageal cancers such as but not limited to, squamous cancer, adenocarcinoma, adenoid cyctic carcinoma, mucoepidermoid carcinoma, adenosquamous carcinoma, sarcoma, melanoma, plasmacytoma, verrucous carcinoma, and oat cell (small cell) carcinoma; stomach cancers such as but not limited to, adenocarcinoma, fungating (polypoid), ulcerating, superficial spreading, diffusely spreading, malignant lymphoma, liposarcoma, fibrosarcoma, and carcinosarcoma; colon cancers; KRAS mutated colorectal cancer; colon carcinoma; rectal cancers; liver cancers such as but not limited to hepatocellular carcinoma and hepatoblastoma, gallbladder cancers such as adenocarcinoma; cholangiocarcinomas such as but not limited to pappillary, nodular, and diffuse; lung cancers such as KRAS-mutated non-small cell lung cancer, non-small cell lung cancer, squamous cell carcinoma (epidermoid carcinoma), adenocarcinoma, large-cell carcinoma and small-cell lung cancer; lung carcinoma; testicular cancers such as but not limited to germinal tumor, seminoma, anaplastic, classic (typical), spermatocytic, nonseminoma, embryonal carcinoma, teratoma carcinoma, choriocarcinoma (yolk-sac tumor), prostate cancers such as but not limited to, androgen-independent prostate cancer, androgen-dependent prostate cancer, adenocarcinoma, leiomyosarcoma, and rhabdomyosarcoma; penal cancers; oral cancers such as but not limited to squamous cell carcinoma; basal cancers; salivary gland cancers such as but not limited to adenocarcinoma, mucoepidermoid carcinoma, and adenoidcystic carcinoma; pharynx cancers such as but not limited to squamous cell cancer, and verrucous; skin cancers such as but not limited to, basal cell carcinoma, squamous cell carcinoma and melanoma, superficial spreading melanoma, nodular melanoma, lentigo malignant melanoma, acrallentiginous melanoma; kidney cancers such as but not limited to renal cell cancer, adenocarcinoma, hypernephroma, fibrosarcoma, transitional cell cancer (renal pelvis and/or uterer); renal carcinoma; Wilms' tumor; bladder cancers such as but not limited to transitional cell carcinoma, squamous cell cancer, adenocarcinoma, carcinosarcoma. In addition, cancers include myxosarcoma, osteogenic sarcoma, endotheliosarcoma, lymphangioendotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma and papillary adenocarcinomas.

In certain embodiments cancers that can be prevented and/or treated in accordance with the present invention include, the following: pediatric solid tumor, Ewing's sarcoma, Wilms tumor, neuroblastoma, neurofibroma, carcinoma of the epidermis, malignant melanoma, cervical carcinoma, colon carcinoma, lung carcinoma, renal carcinoma, breast carcinoma, breast sarcoma, metastatic breast cancer, HIV-related Kaposi's sarcoma, prostate cancer, androgen-independent prostate cancer, androgen-dependent prostate cancer, neurofibromatosis, lung cancer, non-small cell lung cancer, KRAS-mutated non-small cell lung cancer, malignant melanoma, melanoma, colon cancer, KRAS-mutated colorectal cancer, glioblastoma multiforme, renal cancer, kidney cancer, bladder cancer, ovarian cancer, hepatocellular carcinoma, thyroid carcinoma, rhabdomyosarcoma, acute myeloid leukemia, and multiple myeloma.

In certain embodiments, cancers and conditions associated therewith that are prevented and/or treated in accordance with the present invention are breast carcinomas, lung carcinomas, gastric carcinomas, esophageal carcinomas, colorectal carcinomas, liver carcinomas, ovarian carcinomas, thecomas, arrhenoblastomas, cervical carcinomas, endometrial carcinoma, endometrial hyperplasia, endometriosis, fibrosarcomas, choriocarcinoma, head and neck cancer, nasopharyngeal carcinoma, laryngeal carcinomas, hepatoblastoma, Kaposi's sarcoma, melanoma, skin carcinomas, hemangioma, cavernous hemangioma, hemangioblastoma, pancreas carcinomas, retinoblastoma, astrocytoma, glioblastoma, Schwannoma, oligodendroglioma, medulloblastoma, neuroblastomas, rhabdomyosarcoma, osteogenic sarcoma, leiomyosarcomas, urinary tract carcinomas, thyroid carcinomas, Wilm's tumor, renal cell carcinoma, prostate carcinoma, abnormal vascular proliferation associated with phakomatoses, edema (such as that associated with brain tumors), or Meigs' syndrome. In specific embodiment, the cancer an astrocytoma, an oligodendroglioma, a mixture of oligodendroglioma and an astrocytoma elements, an ependymoma, a meningioma, a pituitary adenoma, a primitive neuroectodermal tumor, a medullblastoma, a primary central nervous system (CNS) lymphoma, or a CNS germ cell tumor.

In specific embodiments, the cancer treated in accordance with the present invention is an acoustic neuroma, an anaplastic astrocytoma, a glioblastoma multiforme, or a meningioma.

In other specific embodiments, the cancer treated in accordance with the present invention is a brain stem glioma, a craniopharyngioma, an ependyoma, a juvenile pilocytic astrocytoma, a medulloblastoma, an optic nerve glioma, primitive neuroectodermal tumor, or a rhabdoid tumor.

Preparation of Compound 3

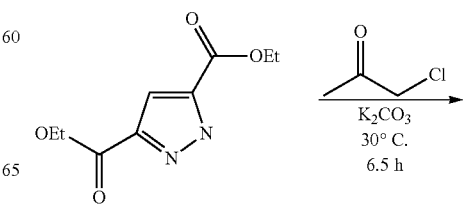

-continued

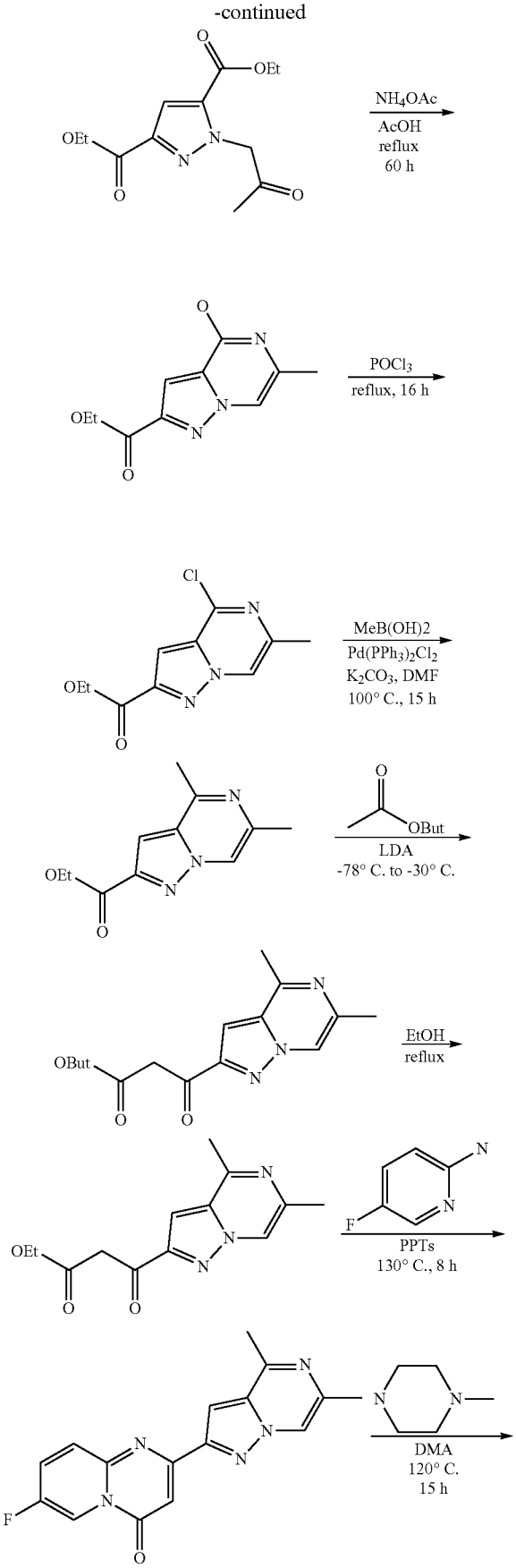

Step A: To a solution of diethyl 1H-pyrazole-3,5-dicarboxylate (10.0 g, 47 mmol) and chloroacetone (3.76 mL, 47 mmol) in acetone (200 mL) was added potassium carbonate (7.2 g, 52 mmol). After heating at 30° C. for 6 h, the mixture was concentrated to remove the volatiles. The residue was taken into EtOAc and washed with water. The organics were dried over MgSO4 and concentrated to give diethyl 1-(2-oxopropyl)-1H-pyrazole-3,5-dicarboxylate as a light brown solid, which was used directly in the next step, MS m/z 269.1 [M+H]+.

Step B: To a solution of diethyl 1-(2-oxopropyl)-1H-pyrazole-3,5-dicarboxylate (~47 mmol) in acetic acid (300 mL) was added ammonium acetate (72 g, 940 mmol). After refluxing for 48 h, the mixture was concentrated to minimum volume and diluted with water. The precipitate was filtered, washed with water and MeCN to give ethyl 4-hydroxy-6-methylpyrazolo[1,5-a]pyrazine-2-carboxylate as a tan solid (6.7 g, 64%), MS m/z 222.1 [M+H]+.

Step C: A mixture of ethyl 4-hydroxy-6-methylpyrazolo[1,5-a]pyrazine-2-carboxylate (7.18 g, 32.5 mmol) in POCl3 (80 mL) was refluxed for 15 h. The dark mixture was concentrated and washed with MeCN to give ethyl 4-chloro-6-methylpyrazolo[1,5-a]pyrazine-2-carboxylate (5.197 g) as an off-white solid. The filtrate was concentrated and chromatographed to give an additional 1.42 g product (6.617 g, 85%) MS m/z 240.1 [M+H]+, 242.1 [M+2+H]+.

Step D: A mixture of ethyl 4-chloro-6-methylpyrazolo[1,5-a]pyrazine-2-carboxylate (5.197 g, 21.7 mmol), MeB(OH)2 (3.90 g, 65.1 mmol), K2CO3 (14.8 g, 107.5 mmol) and Pd(PPh3)2Cl2 in (456 mg, 0.65 mmol) DMF (100 mL) was degassed and heated under N2 for 15 h. The mixture was concentrated on a rotovap to remove most of the DMF and washed with water. The residue was chromatographed (2% to 5% MeOH in CH2Cl2) to give ethyl 4,6-dimethylpyrazolo[1,5-a]pyrazine-2-carboxylate as a yellow solid (3.90 g, 82%), MS m/z 220.1 [M+H]+; 1H NMR (500 MHz, DMSO-d6): δ 8.54 (1H, s), 7.49 (1H, s), 4.36 (2H, q, J=7.2 Hz), 2.70 (3H, s), 2.42 (3H, s), 1.34 (3H, t, J=7.2 Hz).

Step E: To a solution of t-butyl acetate (1.63 mL, 12.1 mmol) in THF (50 mL) at −78° C. was added LDA (1.5 M, 0.97 mL, 14.5 mmol). After 0.5 h, the solution was cannulated to a solution of ethyl 4,6-dimethylpyrazolo[1,5-a]pyrazine-2-carboxylate (1.33 g, 6.07 mmol) in THF (100 mL) at −30° C. After 1 h, the mixture was quenched with saturated NH4Cl, adjusted to pH 5-6 and extracted with EtOAc. The combined organics were dried and concentrated. The residue was chromatographed (2% to 4% MeOH/CH2Cl2) to give t-butyl 3-(4,6-dimethylpyrazolo[1,5-a]pyrazin-2-yl)-3-oxopropanoate as a yellow oil (1.696 g, 97%), MS m/z 290.2 [M+H]+; 1H NMR (500 MHz, DMSO-d6): δ 8.57 (1H, s), 7.50 (1H, s), 4.02 (2H, s), 2.70 (3H, s), 2.43 (3H, s), 1.38 (9H, s).

Step F: A solution of t-butyl 3-(4,6-dimethylpyrazolo[1,5-a]pyrazin-2-yl)-3-oxopropanoate (4.86 g, 16.8 mmol) in EtOH (30 mmol) was heated at 120° C. in a capped tube. After 1 h, the solution was cooled to rt and the volatiles were removed to give ethyl 3-(4,6-dimethylpyrazolo[1,5-a]pyrazin-2-yl)-3-oxopropanoate as a yellow solid (4.44 g, 98%), MS m/z 262.2 [M+H]+.

Step G: A mixture of 2-amino-5-fluoro-pyridine (134 mg, 1.2 mmol), ethyl 3-(4,6-dimethylpyrazolo[1,5-a]pyrazin-2-yl)-3-oxopropanoate (261 mg, 1.0 mmol) and PPTs (12.6 mg, 0.05 mmol) was heated at 130° C. After 8 h, the mixture was cooled to rt and chromatographed to give 2-(4,6-dimethylpyrazolo[1,5-a]pyrazin-2-yl)-7-fluoro-4H-pyrido[1,2-a]pyrimidin-4-one as a yellow solid (220 mg, 71%). MS m/z 310.2 [M+H]+; 1H NMR (500 MHz, DMSO-d6): δ 8.97-8.95 (1H, m), 8.55 (1H, s), 8.16-8.12 (1H, m), 7.87-7.85 (1H, m), 7.56 (1H, s), 7.03 (1H, s), 2.73, (3H, s), 2.43 (3H, s).

Step H: 2-(4,6-dimethylpyrazolo[1,5-a]pyrazin-2-yl)-7-fluoro-4H-pyrido[1,2-a]pyrimidin-4-one (309 mg, 1.0 mmol) and piperazine (1.1 mL, 10 mmol) in DMA (1.0 mL) was heated at 120° C. After 15 h, the volatiles were removed and the residue was washed with MeCN to give the title compound as a yellow solid (313 mg, 80%). M.P. 254-256° C.; MS m/z 390.4 [M+H]+; 1H NMR (500 MHz, DMSO-d6): δ 8.55 (1H, s), 8.27 (1H, d, J=2.7 Hz), 8.12 (1H, dd, J=2.8 Hz, 9.7 Hz), 7.71 (1H, d, J=9.7 Hz), 7.54 (1H, s), 6.95 (1H, s), 3.25 (4H, m), 2.72 (3H, s), 2.51 (4H, m, obscured by DMSO-d6), 2.43 (3H, s), 2.25 (3H, s).

Additional compounds disclosed herein may be prepared according to the above example by substituting the appropriate starting materials, reagents and reaction conditions.

WO 2013/119916 discloses additional compounds which can be used for prophylaxis or treatment of cancer by FoxM1 splicing modification. WO 2013/119916 is hereby included by reference.

The term "M.P." represents "Melting Point (° C.)," the term "MS" represents "Mass Spectroscopy Peak(s) m/z [M+H]$^+$, [M+2+H]$^+$, [M−H]$^−$ or [M+2−H]$^−$," the term "D" represents "Decomposition/Decomposed".

| Compound | Compound Name | M.P. | MS |
|---|---|---|---|
| 1 | 2-(4,6-dimethylpyrazolo[1,5-a]pyrazin-2-yl)-7-(1-ethylpiperidin-4-yl)-9-methyl-4H-pyrido[1,2-a]pyrimidin-4-one | 231-240 | 417.4 |
| 2 | 2-(4-ethyl-6-methylpyrazolo[1,5-a]pyrazin-2-yl)-9-methyl-7-(1,2,3,6-tetrahydropyridin-4-yl)-4H-pyrido[1,2-a]pyrimidin-4-one | 265 (D) | 401.3 |
| 3 | 2-(4,6-dimethylpyrazolo[1,5-a]pyrazin-2-yl)-7-(4-methylpiperazin-1-yl)-4H-pyrido[1,2-a]pyrimidin-4-one | 254-256 | 390.4 |
| 4 | 2-(4,6-dimethylpyrazolo[1,5-a]pyrazin-2-yl)-7-(piperazin-1-yl)-4H-pyrido[1,2-a]pyrimidin-4-one | 195-200 | 376.5 |

EXAMPLES

Example 1: Cpds. Induce Alternative Splicing of FoxM1 Towards FoxM1A

Figure 1C:
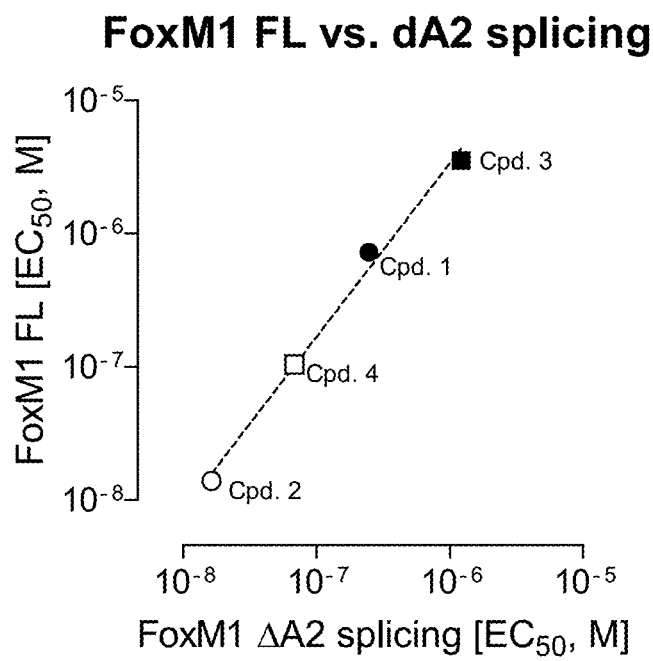

To investigate an effect on splicing of FoxM1, human fibroblasts were treated for 24 hours with cpds. 1-4 in dose response, and analysed by RT-qPCR for presence of mRNA including (FoxM1A) or excluding (FoxM1B/C) the Δ9 exon. The resulting dose response curves were fitted to a Hill binding equation. FIG. 1A shows that all cps. increased expression of the FoxM1 mRNA including exon 9, and $EC_{50}$ values were calculated to 0.246, 0.016, 1.210 and 0.068 uM for cpds. 1, 2, 3 and 4, respectively. Correspondingly, the mRNAs for the FoxM1B/C isoforms lacking exon 9 (Δ9 versions) declined with $EC_{50}$ values of 0.724, 0.014, 3.541 and 0.104 uM for cpds. 1, 2, 3 and 4, respectively. Correlation analysis of the $EC_{50}$ values for upregulation of FoxM1A and downregulation of FoxM1B/C revealed an excellent linear correlation ($r^2$=0.992) with no obvious shift from the line of identity (FIG. 1C). The data suggest a close and direct functional relation of upregulation of FoxM1A and downregulation of FoxM1B/C.

Example 2: Alternative Splicing Towards FoxM1A Induces Cytotoxicity

Figure 2A:
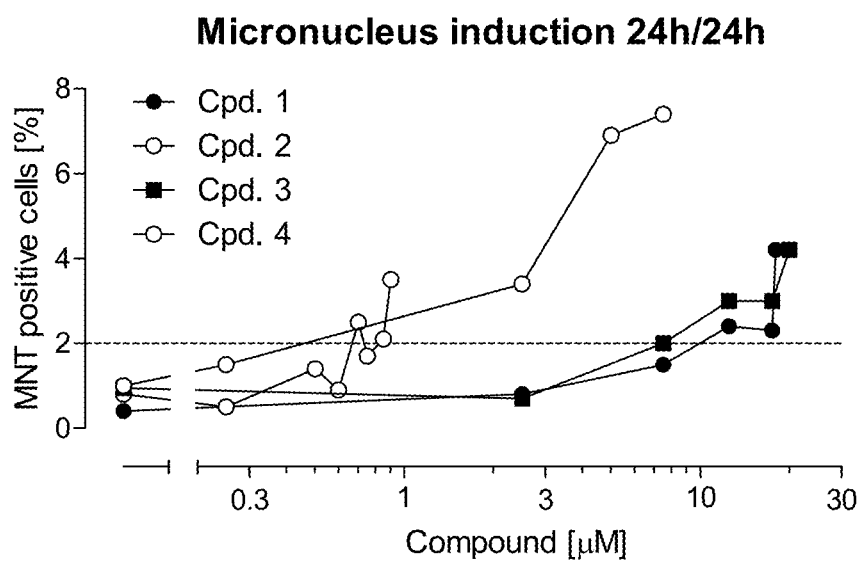
FIGS. 2A, 2B and 2C. Induction of proliferation arrest and cell death by cpds. Alternating FoxM1 splicing towards FoxM1A in fibroblasts. Human fibroblasts were incubated with cpds. 1-4 at different doses for 5 days (120 hours), and changes in cellular impedance (Cell Index) were assessed online. Data are expressed as delta Cell Index after normalization for the starting value of each well. Data at 72, 96 and 120 hour time points (see arrows) were averaged for quantification.
Figure 2B:
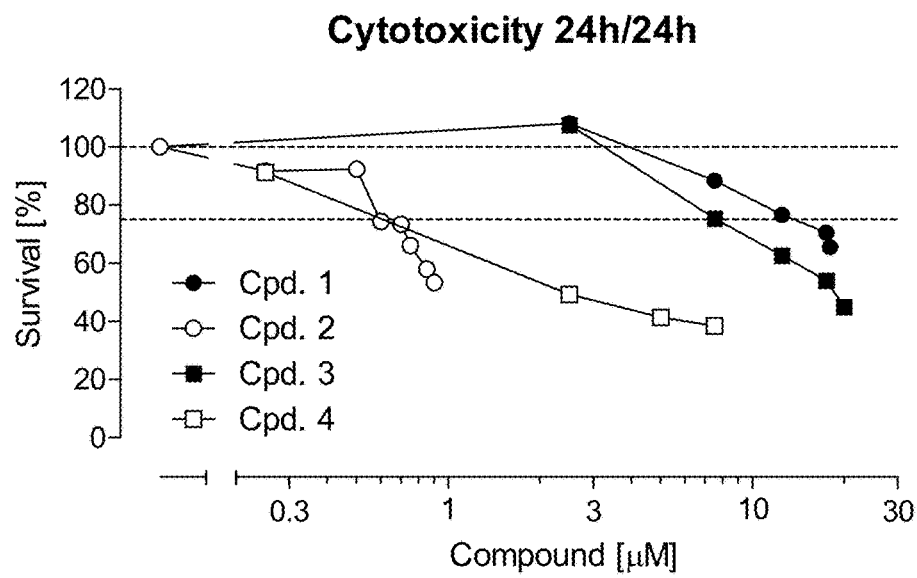
Figure 2C:
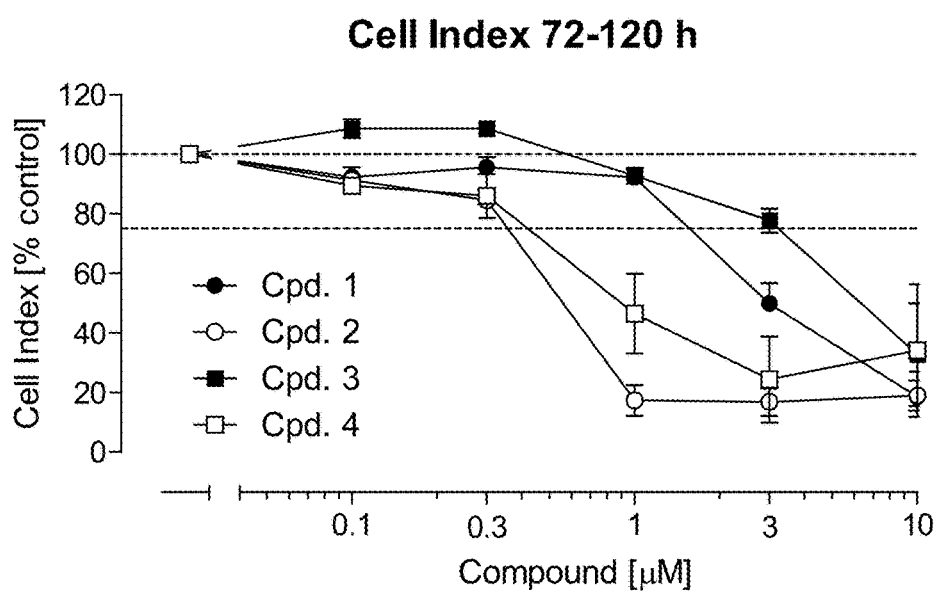

For investigation of the effect of altered FoxM1 expression on micronucleus induction (MNT) and and cell survival, human fibroblasts were treated for up to 120 hours with cpds. 1-4 in dose response, and MNT, cytotoxicity or Cell Index were assessed on the xCELLigence platform, monitoring proliferation rates and cell death online. To define a quantitative measure for cytotoxic effects, a 2% cut-off for MNT induction (FIG. 2A), a 75% cut-off for cell survival ($EC_{75\%}$), and a 75% cut-off was estimated ($ED_{75\%}$). Cpd. 2 and 4 were most potent in MNT, cytotoxicity and reduction of Cell Index (FIGS. 2A, 2B and 2C, respectively). The data suggest that induction of alternative splicing of FoxM1 towards FoxM1A induced slowing of proliferation and cell death.

Example 3: Alternative Splicing of FoxM1 Correlates with Cytotoxicity

Figure 3A:
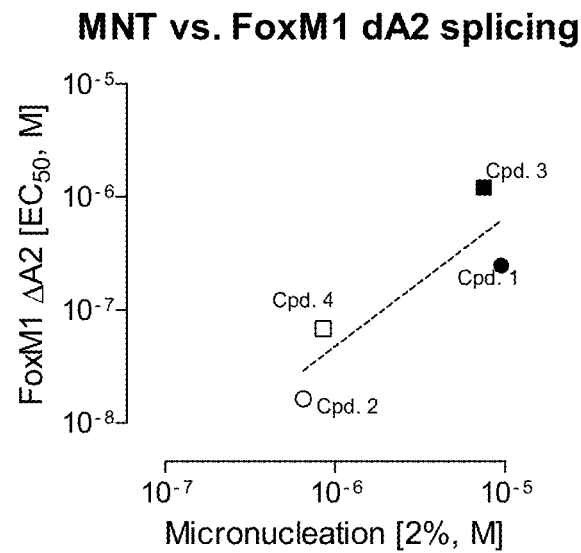
FIGS. 3A, 3B and 3C. Induction of alternative splicing towards FoxM1A correlates with impact on micronucleus induction and cell death in fibroblasts. EC50 values for downregulation of FoxM1 ΔA2 variants and 2%, EC75% and ED75% for MNT, cytotoxicity and Cell Index obtained in FIG. 1A were correlated.
Figure 3B:
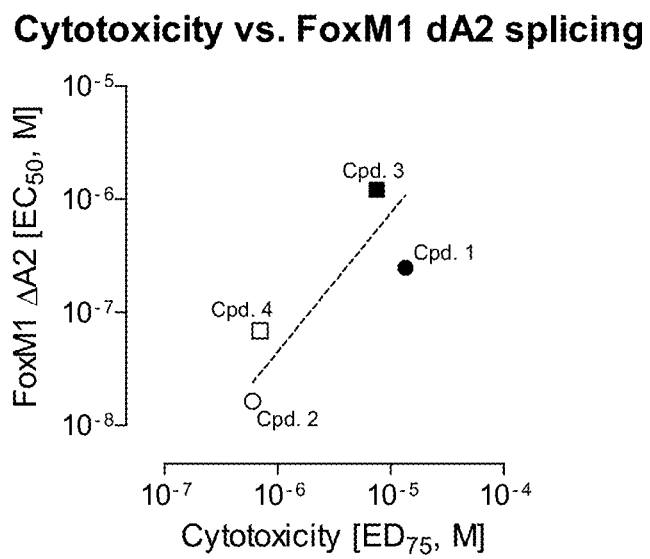
Figure 3C:
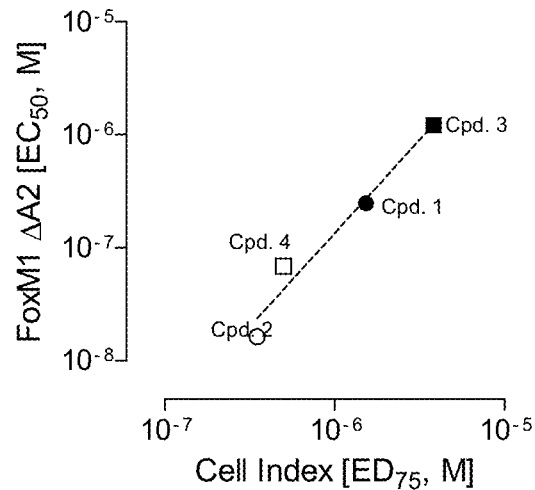

Correlation of the 2%, $EC_{75\%}$ and $ED_{75\%}$ values for the induction in MNT, cytotoxicity or reduction in Cell Index to the $EC_{50}$ for FoxM1B/C reduction (FIGS. 3A, 3B and 3C, respectively) revealed excellent linear correlations, best for the Cell Index ($r^2$=0.963). Thereby, a ~10-fold shift in activity indicated that concentrations of 10-fold above the $EC_{50}$ for FoxM1B/C reduction were required to reach the $ED_{75\%}$ (FIG. 3C).

Example 4: Alternative Splicing of FoxM1 Correlates with Cytotoxicity

Figure 4A:
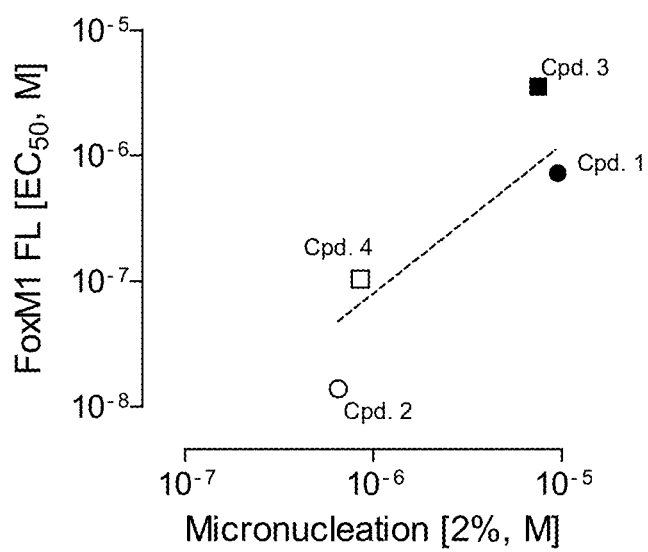
FIGS. 4A, 4B and 4C. Induction of alternative splicing towards FoxM1B/C correlates with impact on micronucleus induction and cell death in fibroblasts. EC50 values for upregulation of FoxM1 FL variant and 2%, EC75% and ED75% for MNT, cytotoxicity and Cell Index, respectively, obtained in FIG. 1B were correlated.
Figure 4B:
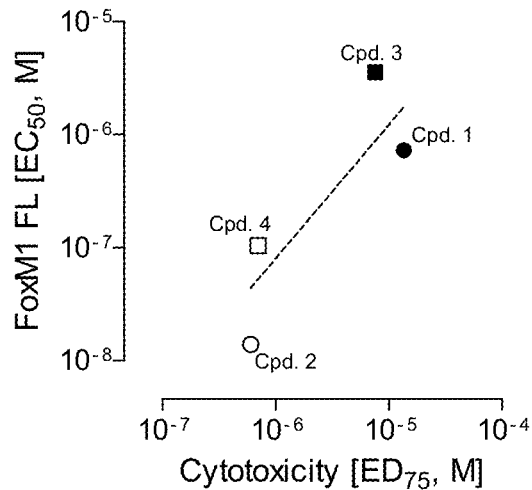
Figure 4C:
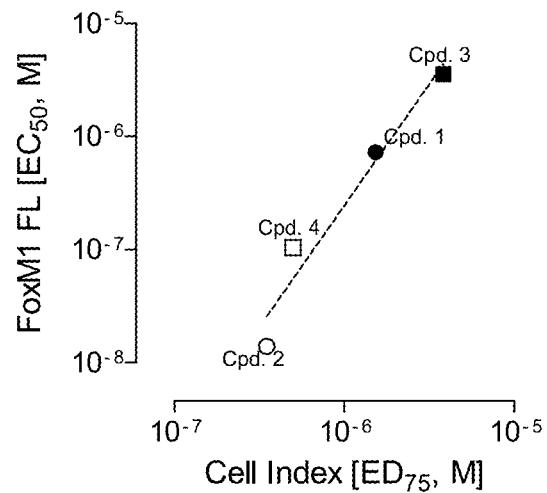

Correlation of the 2%, $EC_{75\%}$ and $ED_{75\%}$ values for the induction in MNT, cytotoxicity or reduction in Cell Index to the $EC_{50}$ for FoxM1B/C reduction (FIGS. 4A, 4B and 4C, respectively) revealed excellent linear correlations, best for the Cell Index ($r^2$=0.951), and a 10- to 15-fold shift in the activity indicated that concentrations of 10- to 15-fold above the $EC_{50}$ for FoxM1A induction were required to reach the $ED_{75\%}$ (FIG. 4C).

The data of examples 3 and 4 suggest that a >90 shift in FoxM1 splicing from FoxM1B/C towards FoxM1A is required to induce meaningful reduction in Cell Index as measure for cell proliferation and survival.

Example 5: Increase of FoxM1A Protein Correlates with Cytotoxicity

Figure 5A:
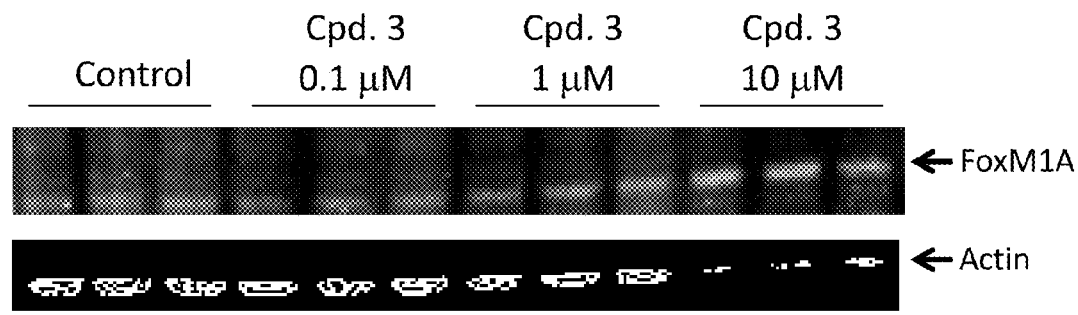
FIGS. 5A, 5B and 5C. Upregulation of FoxM1A protein correlates with cytotoxicity in myoblasts. Human myoblasts were treated with cpd. 3 (0.1, 1 and 10 µM) for 5 days under proliferating conditions (in the presence of serum), and total protein extracts analyzed by SDS PAGE and Western Blot for FoxM1A and actin protein levels.
Figure 5B:
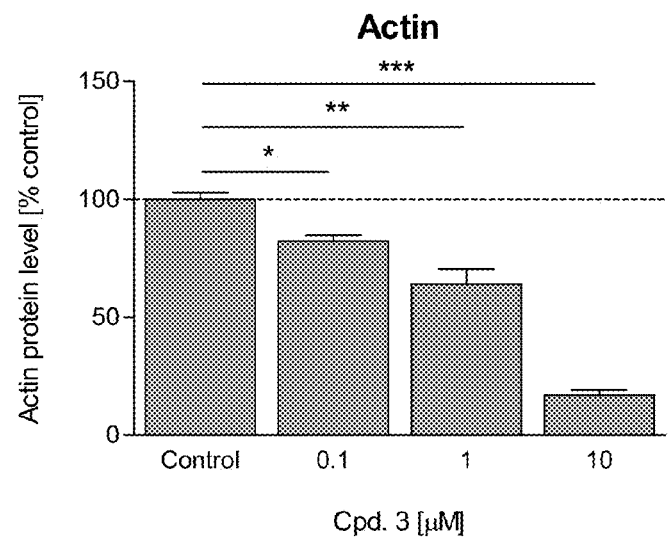
Figure 5C:
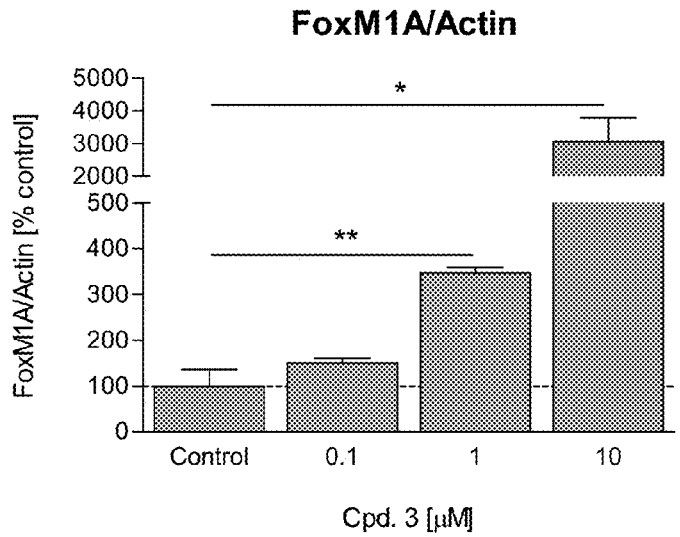

To assess if alternative splicing of FoxM1 towards FoxM1A results in meaningful changes in the protein levels and cell death, human primary myoblasts were treated under proliferating conditions to modulate FoxM1 expression and evaluate its consequence. Under proliferative conditions, FoxM1A was detectable by Western Blot, but at low concentrations (FIG. 4A). Treatment with cpd. 3 at doses up to 10 µM strongly reduced protein levels of actin, a direct marker of cell numbers, but increased protein levels of FoxM1A (FIG. 5A). Quantitative analysis of protein levels indicated that actin was reduced by 6-fold compared to controls (FIG. 5B). When normalized to actin, FoxM1A protein levels increased by 30-fold at the highest dose (FIG. 5C). The data suggest that in proliferating myoblasts, alternative splicing towards FoxM1A increased FoxM1A protein and induced cell death.

Example 6: No Change of FoxM1A Protein in Non-Proliferative Conditions

Figure 6A:
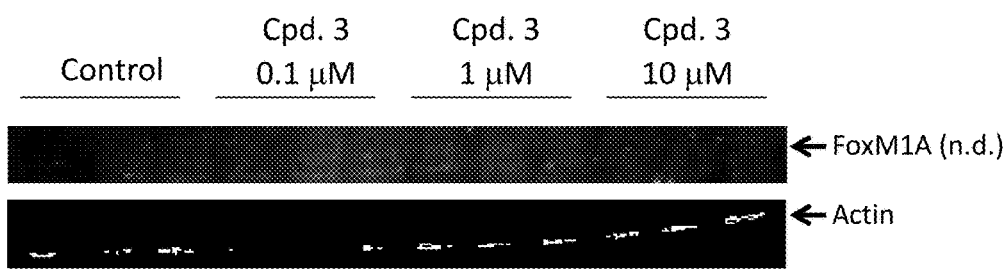
FIGS. 6A and 6B. No change in FoxM1A protein and no cytotoxicity in non-proliferating myoblasts. Human myoblasts were treated with cpd. 3 (0.1, 1 and 10 µM) for 5 days under differentiating conditions (in the absence of serum), and total protein extracts analyzed by SDS PAGE and Western Blot for FoxM1A and actin protein levels.
Figure 6B:
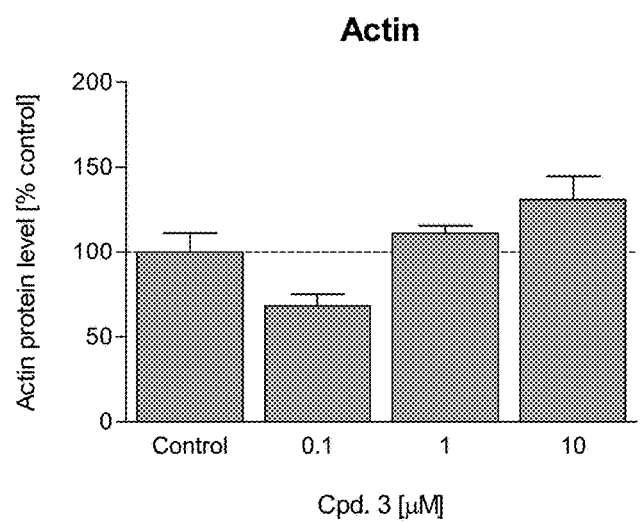

To assess if alternative splicing of FoxM1 towards FoxM1A is present also in cells that are not proliferating, the same human primary myoblasts were differentiated to investigate if FoxM1 expression is also present and can be modulated similarly under those conditions. Under differentiating conditions, FoxM1A was undetectable by Western Blot (FIG. 6A). Treatment with cpd. 3 at doses up to 10 µM did not show any reduction in protein levels of actin as marker of cell numbers (FIG. 6A). Quantitative analysis of protein levels indicated that actin was not altered compared to controls (FIG. 6B), whereas FoxM1A levels normalized to actin was undetectable. The data suggest that FoxM1A expression is restricted to proliferating cells, and alternative splicing towards FoxM1A does not induce cell death in cells that are not proliferating.

Example 7: Increase of FoxM1A Protein Induces Cytotoxicity in Breast Cancer Cells Upregulation of FoxM1A protein correlates with cytotoxicity in breast cancer cells. Human BT474 breast cancer cells were treated with cpd. 2 at 10 µM for 1 or 2 days under proliferating conditions (in the presence of serum), and total protein extracts analyzed by SDS PAGE and Western Blot for FoxM1A and actin protein levels. To assess if increase in FoxM1A protein by alternative splicing of FoxM1 towards FoxM1A induces cell death in a cancer condition, human breast cancer cells (BT474) were treated to modulate FoxM1 expression, and FoxM1A protein levels were assessed at day 1 and 2 of treatment. On day 1 and 2 under control conditions, FoxM1A was detectable by Western Blot, but at low concentrations. Treatment with cpd. 2 at 10 µM did not have any effect on FoxM1A protein but slightly reduced actin protein on day 1, but strongly reduced actin protein on day 2, with a concomitant increase in FoxM1A protein levels. Quantitative analysis of protein levels indicated that actin was reduced on day 1 by 18%, and by more than 90% on day 2 by treatment with cpd. 2 at 10 µM, whereas FoxM1A levels were increased in the same samples by nearly 3-fold. When normalized to actin, FoxM1A protein levels increased by 28-fold by treatment with cpd. 2 at 10 µM. The data suggest that in breast cancer cells, alternative splicing towards FoxM1A increased FoxM1A protein and induced cell death. Data represent means±SEM of 3 independent observations. Statistical comparison was performed by one-way ANOVA followed by Dunnet's post-hoc test. *, $p<0.05$, ***, $p<0.001$.

Methods

Monitoring Expression Levels of FoxM1 Splice Variants Using Real-Time Quantitative PCR.

Fibroblasts, at 10000 cells per $cm^2$ were treated with varying doses of compounds (0.01-10 µM) for 24 hours. RNA extraction was performed as per instructions mentioned in the Ambion® Cells-to-CT™ Kits from Applied Biosystems®. RNA samples were frozen at −20° C. until further analysis. Relative expression levels of FoxM1A or FoxM1B/C along with GAPDH for internal control, was measured using one-step multiplex reverse transcription-polymerase chain reaction (RT-PCR). TaqMan® FAM probes were used for relative quantitation of FoxM1A or FoxM1B/C expression levels and TaqMan® VIC probes were used for relative quantitation of human GAPDH levels. The fidelity of the amplification methods was determined using the ΔΔCt relative quantification method for quantitative PCR.

Monitoring Real-Time Effects on Fibroblast Cell Proliferation as Well as Toxicity Fibroblasts at 10000 cells per $cm^2$ were treated with varying doses of compounds (0.1-10 µM) for 5 days in an xCELLigence E Plate-16 format. Plates were transferred onto the xCELLigence RTCA-DP instrument placed in the 37° C., 5% $CO_2$ incubator and background impedance measurement of all the wells was recorded. Fibroblasts were seeded into the wells and incubated for approximately 5 hours to facilitate even spreading and stabilization of the cells. Changes in impedance at the gold microelectrodes covering the under-surface of the membranes as the cells attach and spread was measured and recorded every 30 minutes over 120 hours (5 days). Impedance was represented by the relative and dimensionless parameter named Cell Index (CI). Cell Index values=Zt−Zi/15 [Ohm]; where Zi=initial impedance at the start of the experiment and Zt=individual time-points during the experiment (A. K. Bosserhoff, L. Ellmann, S. Kuphal. S: Melanoblasts in culture as an in vitro system to determine molecular changes in melanoma. 2011. Experimental Dermatology, 20, 435-440). The values obtained in the initial six hours were annulled from the slope-calculations to take into considerations any variations observed due to the differences, if any, in the attachment capabilities of cells in response to the treatments.

Human Myoblast or Breast Cancer Cell Culture and Western Blot Analysis

Human myoblasts were acquired from ECACC, BT474 cells were obtained from ATCC, and were cultivated according to supplier protocols. For experimental purpose, human myoblasts were cultivated for 5 days and were treated with varying doses of compounds (0.1-10 µM). BT474 cells were cultivated for up to 2 days and treated with compounds at 10 µM. For Western blot analyses, myoblast cells treated over 5 days or BT474 cells treated for 2 days were lysed in boiling Laemmli buffer (Bio-Rad) containing 100 mM dithiothreitol. SDS PAGE blots were probed with rabbit-anti FoxM1 antibody (Cell Signaling Technology, 1:1000), goat anti-Actin (Santa Cruz Biotechnology, 1:20000) and Alexa680/800 secondary antibodies (Molecular Probes, 1:10,000). Fluorescence was acquired with the Odyssey imaging system (Licor Biosciences), FoxM1A intensity was normalized for actin. Data were analyzed using GraphPad software.

The invention claimed is:

1. A method for the treatment of cancer in a subject in need thereof comprising administering to the subject an effective amount of a compound selected from the group consisting of:
- 2-(4,6-dimethylpyrazolo[1,5-a]pyrazin-2-yl)-7-(1-ethyl-piperidin-4-yl)-9-methyl-4H-pyrido[1,2-a]pyrimidin-4-one;
- 2-(4-ethyl-6-methylpyrazolo[1,5-a]pyrazin-2-yl)-9-methyl-7-(1,2,3,6-tetrahydropyridin-4-yl)-4H-pyrido[1,2-a]pyrimidin-4-one;
- 2-(4,6-dimethylpyrazolo[1,5-a]pyrazin-2-yl)-7-(4-methylpiperazin-1-yl)-4H-pyrido[1,2-a]pyrimidin-4-one; and
- 2-(4,6-dimethylpyrazolo[1,5-a]pyrazin-2-yl)-7-(piperazin-1-yl)-4H-pyrido[1,2-a]pyrimidin-4-one, or a pharmaceutically acceptable salt thereof.

2. The method of claim 1, wherein the cancer is a cancer expressing a FoxM1 gene.

3. The method of claim 1, wherein the subject is a human.

4. The method of claim 3, wherein the cancer is a cancer expressing a human FoxM1 gene.

5. The method of claim 1, wherein the cancer is selected from the group consisting of cancers of the liver, prostate, brain, breast, lung, colon, pancreas, skin, cervix, ovary, mouth, blood and nervous system.

6. The method of claim 1, wherein the compound is 2-(4,6-dimethylpyrazolo[1,5-a]pyrazin-2-yl)-7-(1-ethylpiperidin-4-yl)-9-methyl-4H-pyrido[1,2-a]pyrimidin-4-one, or a pharmaceutically acceptable salt thereof.

7. The method of claim 1, wherein the compound is 2-(4-ethyl-6-methylpyrazolo[1,5-a]pyrazin-2-yl)-9-methyl-7-(1,2,3,6-tetrahydropyridin-4-yl)-4H-pyrido[1,2-a]pyrimidin-4-one, or a pharmaceutically acceptable salt thereof.

8. The method of claim 1, wherein the compound is 2-(4,6-dimethylpyrazolo[1,5-a]pyrazin-2-yl)-7-(4-methylpiperazin-1-yl)-4H-pyrido[1,2-a]pyrimidin-4-one, or a pharmaceutically acceptable salt thereof.

9. The method of claim 1, wherein the compound is 2-(4,6-dimethylpyrazolo[1,5-a]pyrazin-2-yl)-7-(piperazin-1-yl)-4H-pyrido[1,2-a]pyrimidin-4-one, or a pharmaceutically acceptable salt thereof.

* * * * *

SEQUENCE LISTING

<160> NUMBER OF SEQ ID NOS: 9

<210> SEQ ID NO 1
<211> LENGTH: 801
<212> TYPE: PRT
<213> ORGANISM: Homo sapiens

<400> SEQUENCE: 1

Met Lys Thr Ser Pro Arg Arg Pro Leu Ile Leu Lys Arg Arg Arg Leu
1               5                   10                  15

Pro Leu Pro Val Gln Asn Ala Pro Ser Glu Thr Ser Glu Glu Glu Pro
            20                  25                  30

Lys Arg Ser Pro Ala Gln Gln Glu Ser Asn Gln Ala Glu Ala Ser Lys
        35                  40                  45

Glu Val Ala Glu Ser Asn Ser Cys Lys Phe Pro Ala Gly Ile Lys Ile
    50                  55                  60

Ile Asn His Pro Thr Met Pro Asn Thr Gln Val Val Ala Ile Pro Asn
65                  70                  75                  80

Asn Ala Asn Ile His Ser Ile Ile Thr Ala Leu Thr Ala Lys Gly Lys
                85                  90                  95

Glu Ser Gly Ser Ser Gly Pro Asn Lys Phe Ile Leu Ile Ser Cys Gly
            100                 105                 110

Gly Ala Pro Thr Gln Pro Pro Gly Leu Arg Pro Gln Thr Gln Thr Ser
        115                 120                 125

Tyr Asp Ala Lys Arg Thr Glu Val Thr Leu Glu Thr Leu Gly Pro Lys
    130                 135                 140

Pro Ala Ala Arg Asp Val Asn Leu Pro Arg Pro Pro Gly Ala Leu Cys
145                 150                 155                 160

Glu Gln Lys Arg Glu Thr Cys Ala Asp Gly Glu Ala Ala Gly Cys Thr
                165                 170                 175

Ile Asn Asn Ser Leu Ser Asn Ile Gln Trp Leu Arg Lys Met Ser Ser
            180                 185                 190

Asp Gly Leu Gly Ser Arg Ser Ile Lys Gln Glu Met Glu Glu Lys Glu
        195                 200                 205

Asn Cys His Leu Glu Gln Arg Gln Val Lys Val Glu Glu Pro Ser Arg
    210                 215                 220

Pro Ser Ala Ser Trp Gln Asn Ser Val Ser Glu Arg Pro Pro Tyr Ser
225                 230                 235                 240

Tyr Met Ala Met Ile Gln Phe Ala Ile Asn Ser Thr Glu Arg Lys Arg
                245                 250                 255

Met Thr Leu Lys Asp Ile Tyr Thr Trp Ile Glu Asp His Phe Pro Tyr
            260                 265                 270

Phe Lys His Ile Ala Lys Pro Gly Trp Lys Asn Ser Ile Arg His Asn
        275                 280                 285

Leu Ser Leu His Asp Met Phe Val Arg Glu Thr Ser Ala Asn Gly Lys
    290                 295                 300

Val Ser Phe Trp Thr Ile His Pro Ser Ala Asn Arg Tyr Leu Thr Leu
305                 310                 315                 320

Asp Gln Val Phe Lys Pro Leu Asp Pro Gly Ser Pro Gln Leu Pro Glu
                325                 330                 335

His Leu Glu Ser Gln Gln Lys Arg Pro Asn Pro Glu Leu Arg Arg Asn
            340                 345                 350

Met Thr Ile Lys Thr Glu Leu Pro Leu Gly Ala Arg Arg Lys Met Lys
        355                 360                 365

-continued

Pro Leu Leu Pro Arg Val Ser Ser Tyr Leu Val Pro Ile Gln Phe Pro
370                 375                 380

Val Asn Gln Ser Leu Val Leu Gln Pro Ser Val Lys Val Pro Leu Pro
385                 390                 395                 400

Leu Ala Ala Ser Leu Met Ser Ser Glu Leu Ala Arg His Ser Lys Arg
                405                 410                 415

Val Arg Ile Ala Pro Lys Val Phe Gly Glu Gln Val Val Phe Gly Tyr
            420                 425                 430

Met Ser Lys Phe Phe Ser Gly Asp Leu Arg Asp Phe Gly Thr Pro Ile
        435                 440                 445

Thr Ser Leu Phe Asn Phe Ile Phe Leu Cys Leu Ser Val Leu Leu Ala
450                 455                 460

Glu Gly Ile Ala Pro Leu Ser Ser Ala Gly Pro Gly Lys Glu Glu
465                 470                 475                 480

Lys Leu Leu Phe Gly Glu Gly Phe Ser Pro Leu Leu Pro Val Gln Thr
                485                 490                 495

Ile Lys Glu Glu Glu Ile Gln Pro Gly Glu Glu Met Pro His Leu Ala
            500                 505                 510

Arg Pro Ile Lys Val Glu Ser Pro Leu Glu Glu Trp Pro Ser Pro
515                 520                 525

Ala Pro Ser Phe Lys Glu Glu Ser Ser His Ser Trp Glu Asp Ser Ser
530                 535                 540

Gln Ser Pro Thr Pro Arg Pro Lys Lys Ser Tyr Ser Gly Leu Arg Ser
545                 550                 555                 560

Pro Thr Arg Cys Val Ser Glu Met Leu Val Ile Gln His Arg Glu Arg
                565                 570                 575

Arg Glu Arg Ser Arg Ser Arg Arg Lys Gln His Leu Leu Pro Pro Cys
            580                 585                 590

Val Asp Glu Pro Glu Leu Leu Phe Ser Glu Gly Pro Ser Thr Ser Arg
        595                 600                 605

Trp Ala Ala Glu Leu Pro Phe Pro Ala Asp Ser Asp Pro Ala Ser
610                 615                 620

Gln Leu Ser Tyr Ser Gln Glu Val Gly Gly Pro Phe Lys Thr Pro Ile
625                 630                 635                 640

Lys Glu Thr Leu Pro Ile Ser Ser Thr Pro Ser Lys Ser Val Leu Pro
                645                 650                 655

Arg Thr Pro Glu Ser Trp Arg Leu Thr Pro Pro Ala Lys Val Gly Gly
            660                 665                 670

Leu Asp Phe Ser Pro Val Gln Thr Ser Gln Gly Ala Ser Asp Pro Leu
        675                 680                 685

Pro Asp Pro Leu Gly Leu Met Asp Leu Ser Thr Thr Pro Leu Gln Ser
690                 695                 700

Ala Pro Pro Leu Glu Ser Pro Gln Arg Leu Leu Ser Ser Glu Pro Leu
705                 710                 715                 720

Asp Leu Ile Ser Val Pro Phe Gly Asn Ser Ser Pro Ser Asp Ile Asp
                725                 730                 735

Val Pro Lys Pro Gly Ser Pro Glu Pro Gln Val Ser Gly Leu Ala Ala
            740                 745                 750

Asn Arg Ser Leu Thr Glu Gly Leu Val Leu Asp Thr Met Asn Asp Ser
        755                 760                 765

Leu Ser Lys Ile Leu Leu Asp Ile Ser Phe Pro Gly Leu Asp Glu Asp
770                 775                 780

Pro Leu Gly Pro Asp Asn Ile Asn Trp Ser Gln Phe Ile Pro Glu Leu

```
                785                 790                 795                 800
Gln

<210> SEQ ID NO 2
<211> LENGTH: 748
<212> TYPE: PRT
<213> ORGANISM: Homo sapiens

<400> SEQUENCE: 2

Met Lys Thr Ser Pro Arg Arg Pro Leu Ile Leu Lys Arg Arg Arg Leu
1               5                   10                  15

Pro Leu Pro Val Gln Asn Ala Pro Ser Glu Thr Ser Glu Glu Glu Pro
            20                  25                  30

Lys Arg Ser Pro Ala Gln Gln Glu Ser Asn Gln Ala Glu Ala Ser Lys
        35                  40                  45

Glu Val Ala Glu Ser Asn Ser Cys Lys Phe Pro Ala Gly Ile Lys Ile
    50                  55                  60

Ile Asn His Pro Thr Met Pro Asn Thr Gln Val Val Ala Ile Pro Asn
65                  70                  75                  80

Asn Ala Asn Ile His Ser Ile Ile Thr Ala Leu Thr Ala Lys Gly Lys
                85                  90                  95

Glu Ser Gly Ser Ser Gly Pro Asn Lys Phe Ile Leu Ile Ser Cys Gly
            100                 105                 110

Gly Ala Pro Thr Gln Pro Pro Gly Leu Arg Pro Gln Thr Gln Thr Ser
        115                 120                 125

Tyr Asp Ala Lys Arg Thr Glu Val Thr Leu Glu Thr Leu Gly Pro Lys
130                 135                 140

Pro Ala Ala Arg Asp Val Asn Leu Pro Arg Pro Pro Gly Ala Leu Cys
145                 150                 155                 160

Glu Gln Lys Arg Glu Thr Cys Asp Gly Glu Ala Ala Gly Cys Thr Ile
                165                 170                 175

Asn Asn Ser Leu Ser Asn Ile Gln Trp Leu Arg Lys Met Ser Ser Asp
            180                 185                 190

Gly Leu Gly Ser Arg Ser Ile Lys Gln Glu Met Glu Glu Lys Glu Asn
        195                 200                 205

Cys His Leu Glu Gln Arg Gln Val Lys Val Glu Glu Pro Ser Arg Pro
    210                 215                 220

Ser Ala Ser Trp Gln Asn Ser Val Ser Glu Arg Pro Pro Tyr Ser Tyr
225                 230                 235                 240

Met Ala Met Ile Gln Phe Ala Ile Asn Ser Thr Glu Arg Lys Arg Met
                245                 250                 255

Thr Leu Lys Asp Ile Tyr Thr Trp Ile Glu Asp His Phe Pro Tyr Phe
            260                 265                 270

Lys His Ile Ala Lys Pro Gly Trp Lys Asn Ser Ile Arg His Asn Leu
        275                 280                 285

Ser Leu His Asp Met Phe Val Arg Glu Thr Ser Ala Asn Gly Lys Val
    290                 295                 300

Ser Phe Trp Thr Ile His Pro Ser Ala Asn Arg Tyr Leu Thr Leu Asp
305                 310                 315                 320

Gln Val Phe Lys Gln Gln Lys Arg Pro Asn Pro Glu Leu Arg Arg
                325                 330                 335

Asn Met Thr Ile Lys Thr Glu Leu Pro Leu Gly Ala Arg Arg Lys Met
            340                 345                 350

Lys Pro Leu Leu Pro Arg Val Ser Ser Tyr Leu Val Pro Ile Gln Phe
```

```
            355                 360                 365
Pro Val Asn Gln Ser Leu Val Leu Gln Pro Ser Val Lys Val Pro Leu
370                 375                 380

Pro Leu Ala Ala Ser Leu Met Ser Ser Glu Leu Ala Arg His Ser Lys
385                 390                 395                 400

Arg Val Arg Ile Ala Pro Lys Val Leu Leu Ala Glu Glu Gly Ile Ala
                405                 410                 415

Pro Leu Ser Ser Ala Gly Pro Gly Lys Glu Lys Leu Leu Phe Gly
            420                 425                 430

Glu Gly Phe Ser Pro Leu Leu Pro Val Gln Thr Ile Lys Glu Glu
                435                 440                 445

Ile Gln Pro Gly Glu Glu Met Pro His Leu Ala Arg Pro Ile Lys Val
450                 455                 460

Glu Ser Pro Pro Leu Glu Glu Trp Pro Ser Pro Ala Pro Ser Phe Lys
465                 470                 475                 480

Glu Glu Ser Ser His Ser Trp Glu Asp Ser Gln Ser Pro Thr Pro
                485                 490                 495

Arg Pro Lys Lys Ser Tyr Ser Gly Leu Arg Ser Pro Thr Arg Cys Val
                500                 505                 510

Ser Glu Met Leu Val Ile Gln His Arg Glu Arg Glu Arg Ser Arg
                515                 520                 525

Ser Arg Arg Lys Gln His Leu Leu Pro Pro Cys Val Asp Glu Pro Glu
530                 535                 540

Leu Leu Phe Ser Glu Gly Pro Ser Thr Ser Arg Trp Ala Ala Glu Leu
545                 550                 555                 560

Pro Phe Pro Ala Asp Ser Ser Asp Pro Ala Ser Gln Leu Ser Tyr Ser
                565                 570                 575

Gln Glu Val Gly Gly Pro Phe Lys Thr Pro Ile Lys Glu Thr Leu Pro
                580                 585                 590

Ile Ser Ser Thr Pro Ser Lys Ser Val Leu Pro Arg Thr Pro Glu Ser
                595                 600                 605

Trp Arg Leu Thr Pro Pro Ala Lys Val Gly Gly Leu Asp Phe Ser Pro
610                 615                 620

Val Gln Thr Ser Gln Gly Ala Ser Asp Pro Leu Pro Asp Pro Leu Gly
625                 630                 635                 640

Leu Met Asp Leu Ser Thr Thr Pro Leu Gln Ser Ala Pro Pro Leu Glu
                645                 650                 655

Ser Pro Gln Arg Leu Leu Ser Ser Glu Pro Leu Asp Leu Ile Ser Val
                660                 665                 670

Pro Phe Gly Asn Ser Ser Pro Ser Asp Ile Asp Val Pro Lys Pro Gly
                675                 680                 685

Ser Pro Glu Pro Gln Val Ser Gly Leu Ala Ala Asn Arg Ser Leu Thr
                690                 695                 700

Glu Gly Leu Val Leu Asp Thr Met Asn Asp Ser Leu Ser Lys Ile Leu
705                 710                 715                 720

Leu Asp Ile Ser Phe Pro Gly Leu Asp Glu Asp Pro Leu Gly Pro Asp
                725                 730                 735

Asn Ile Asn Trp Ser Gln Phe Ile Pro Glu Leu Gln
                740                 745

<210> SEQ ID NO 3
<211> LENGTH: 763
<212> TYPE: PRT
<213> ORGANISM: Homo sapiens
```

<400> SEQUENCE: 3

```
Met Lys Thr Ser Pro Arg Arg Pro Leu Ile Leu Lys Arg Arg Leu
1               5                   10                  15

Pro Leu Pro Val Gln Asn Ala Pro Ser Glu Thr Ser Glu Glu Glu Pro
            20                  25                  30

Lys Arg Ser Pro Ala Gln Gln Glu Ser Asn Gln Ala Glu Ala Ser Lys
        35                  40                  45

Glu Val Ala Glu Ser Asn Ser Cys Lys Phe Pro Ala Gly Ile Lys Ile
    50                  55                  60

Ile Asn His Pro Thr Met Pro Asn Thr Gln Val Val Ala Ile Pro Asn
65                  70                  75                  80

Asn Ala Asn Ile His Ser Ile Ile Thr Ala Leu Thr Ala Lys Gly Lys
                85                  90                  95

Glu Ser Gly Ser Ser Gly Pro Asn Lys Phe Ile Leu Ile Ser Cys Gly
            100                 105                 110

Gly Ala Pro Thr Gln Pro Pro Gly Leu Arg Pro Gln Thr Gln Thr Ser
        115                 120                 125

Tyr Asp Ala Lys Arg Thr Glu Val Thr Leu Glu Thr Leu Gly Pro Lys
    130                 135                 140

Pro Ala Ala Arg Asp Val Asn Leu Pro Arg Pro Pro Gly Ala Leu Cys
145                 150                 155                 160

Glu Gln Lys Arg Glu Thr Cys Ala Asp Gly Glu Ala Ala Gly Cys Thr
                165                 170                 175

Ile Asn Asn Ser Leu Ser Asn Ile Gln Trp Leu Arg Lys Met Ser Ser
            180                 185                 190

Asp Gly Leu Gly Ser Arg Ser Ile Lys Gln Glu Met Glu Glu Lys Glu
        195                 200                 205

Asn Cys His Leu Glu Gln Arg Gln Val Lys Val Glu Glu Pro Ser Arg
    210                 215                 220

Pro Ser Ala Ser Trp Gln Asn Ser Val Ser Glu Arg Pro Pro Tyr Ser
225                 230                 235                 240

Tyr Met Ala Met Ile Gln Phe Ala Ile Asn Ser Thr Glu Arg Lys Arg
                245                 250                 255

Met Thr Leu Lys Asp Ile Tyr Thr Trp Ile Glu Asp His Phe Pro Tyr
            260                 265                 270

Phe Lys His Ile Ala Lys Pro Gly Trp Lys Asn Ser Ile Arg His Asn
        275                 280                 285

Leu Ser Leu His Asp Met Phe Val Arg Glu Thr Ser Ala Asn Gly Lys
    290                 295                 300

Val Ser Phe Trp Thr Ile His Pro Ser Ala Asn Arg Tyr Leu Thr Leu
305                 310                 315                 320

Asp Gln Val Phe Lys Pro Leu Asp Pro Gly Ser Pro Gln Leu Pro Glu
                325                 330                 335

His Leu Glu Ser Gln Gln Lys Arg Pro Asn Pro Glu Leu Arg Arg Asn
            340                 345                 350

Met Thr Ile Lys Thr Glu Leu Pro Leu Gly Ala Arg Arg Lys Met Lys
        355                 360                 365

Pro Leu Leu Pro Arg Val Ser Ser Tyr Leu Val Pro Ile Gln Phe Pro
    370                 375                 380

Val Asn Gln Ser Leu Val Leu Gln Pro Ser Val Lys Val Pro Leu Pro
385                 390                 395                 400

Leu Ala Ala Ser Leu Met Ser Ser Glu Leu Ala Arg His Ser Lys Arg
```

```
                    405                 410                 415
Val Arg Ile Ala Pro Lys Val Leu Leu Ala Glu Glu Gly Ile Ala Pro
                420                 425                 430

Leu Ser Ser Ala Gly Pro Gly Lys Glu Glu Lys Leu Leu Phe Gly Glu
            435                 440                 445

Gly Phe Ser Pro Leu Leu Pro Val Gln Thr Ile Lys Glu Glu Glu Ile
        450                 455                 460

Gln Pro Gly Glu Met Pro His Leu Ala Arg Pro Ile Lys Val Glu
465                 470                 475                 480

Ser Pro Pro Leu Glu Glu Trp Pro Ser Pro Ala Pro Ser Phe Lys Glu
                485                 490                 495

Glu Ser Ser His Ser Trp Glu Asp Ser Ser Gln Ser Pro Thr Pro Arg
            500                 505                 510

Pro Lys Lys Ser Tyr Ser Gly Leu Arg Ser Pro Thr Arg Cys Val Ser
        515                 520                 525

Glu Met Leu Val Ile Gln His Arg Glu Arg Arg Glu Arg Ser Arg Ser
    530                 535                 540

Arg Arg Lys Gln His Leu Leu Pro Pro Cys Val Asp Glu Pro Glu Leu
545                 550                 555                 560

Leu Phe Ser Glu Gly Pro Ser Thr Ser Arg Trp Ala Ala Glu Leu Pro
                565                 570                 575

Phe Pro Ala Asp Ser Ser Asp Pro Ala Ser Gln Leu Ser Tyr Ser Gln
            580                 585                 590

Glu Val Gly Gly Pro Phe Lys Thr Pro Ile Lys Glu Thr Leu Pro Ile
        595                 600                 605

Ser Ser Thr Pro Ser Lys Ser Val Leu Pro Arg Thr Pro Glu Ser Trp
    610                 615                 620

Arg Leu Thr Pro Pro Ala Lys Val Gly Gly Leu Asp Phe Ser Pro Val
625                 630                 635                 640

Gln Thr Ser Gln Gly Ala Ser Asp Pro Leu Pro Asp Pro Leu Gly Leu
                645                 650                 655

Met Asp Leu Ser Thr Thr Pro Leu Gln Ser Ala Pro Pro Leu Glu Ser
            660                 665                 670

Pro Gln Arg Leu Leu Ser Ser Glu Pro Leu Asp Leu Ile Ser Val Pro
        675                 680                 685

Phe Gly Asn Ser Ser Pro Ser Asp Ile Asp Val Pro Lys Pro Gly Ser
    690                 695                 700

Pro Glu Pro Gln Val Ser Gly Leu Ala Ala Asn Arg Ser Leu Thr Glu
705                 710                 715                 720

Gly Leu Val Leu Asp Thr Met Asn Asp Ser Leu Ser Lys Ile Leu Leu
                725                 730                 735

Asp Ile Ser Phe Pro Gly Leu Asp Glu Asp Pro Leu Gly Pro Asp Asn
            740                 745                 750

Ile Asn Trp Ser Gln Phe Ile Pro Glu Leu Gln
        755                 760

<210> SEQ ID NO 4
<211> LENGTH: 3665
<212> TYPE: DNA
<213> ORGANISM: Homo sapiens
<220> FEATURE:
<221> NAME/KEY: CDS
<222> LOCATION: (284)..(2689)

<400> SEQUENCE: 4
```

-continued

```
tttcaaacag cggaacaaac tgaaagctcc ggtgccagac cccacccccg gccccggccc        60
gggaccccct cccctcccgg gatccccegg ggttcccacc ccgcccgcac cgccggggac       120
ccggccggtc cggcgcgagc ccccgtccgg ggccctggct cggcccccag gttggaggag       180
cccggagccc gccttcggag ctacggccta acggcggcgg cgactgcagt ctggagggtc       240
cacacttgtg attctcaatg gagagtgaaa acgcagattc ata atg aaa act agc       295
                                              Met Lys Thr Ser
                                               1 ccc cgt cgg cca ctg att ctc aaa aga cgg agg ctg ccc ctt cct gtt       343
Pro Arg Arg Pro Leu Ile Leu Lys Arg Arg Arg Leu Pro Leu Pro Val
 5              10                  15                  20 caa aat gcc cca agt gaa aca tca gag gag gaa cct aag aga tcc cct       391
Gln Asn Ala Pro Ser Glu Thr Ser Glu Glu Glu Pro Lys Arg Ser Pro
                25                  30                  35 gcc caa cag gag tct aat caa gca gag gcc tcc aag gaa gtg gca gag       439
Ala Gln Gln Glu Ser Asn Gln Ala Glu Ala Ser Lys Glu Val Ala Glu
         40                  45                  50 tcc aac tct tgc aag ttt cca gct ggg atc aag att att aac cac ccc       487
Ser Asn Ser Cys Lys Phe Pro Ala Gly Ile Lys Ile Ile Asn His Pro
             55                  60                  65 acc atg ccc aac acg caa gta gtg gcc atc ccc aac aat gct aat att       535
Thr Met Pro Asn Thr Gln Val Val Ala Ile Pro Asn Asn Ala Asn Ile
 70                  75                  80 cac agc atc atc aca gca ctg act gcc aag gga aaa gag agt ggc agt       583
His Ser Ile Ile Thr Ala Leu Thr Ala Lys Gly Lys Glu Ser Gly Ser
 85                  90                  95                 100 agt ggg ccc aac aaa ttc atc ctc atc agc tgt ggg gga gcc cca act       631
Ser Gly Pro Asn Lys Phe Ile Leu Ile Ser Cys Gly Gly Ala Pro Thr
                105                 110                 115 cag cct cca gga ctc cgg cct caa acc caa acc agc tat gat gcc aaa       679
Gln Pro Pro Gly Leu Arg Pro Gln Thr Gln Thr Ser Tyr Asp Ala Lys
             120                 125                 130 agg aca gaa gtg acc ctg gag acc ttg gga cca aaa cct gca gct agg       727
Arg Thr Glu Val Thr Leu Glu Thr Leu Gly Pro Lys Pro Ala Ala Arg
         135                 140                 145 gat gtg aat ctt cct aga cca cct gga gcc ctt tgc gag cag aaa cgg       775
Asp Val Asn Leu Pro Arg Pro Pro Gly Ala Leu Cys Glu Gln Lys Arg
 150                 155                 160 gag acc tgt gca gat ggt gag gca gca ggc tgc act atc aac aat agc       823
Glu Thr Cys Ala Asp Gly Glu Ala Ala Gly Cys Thr Ile Asn Asn Ser
165                 170                 175                 180 cta tcc aac atc cag tgg ctt cga aag atg agt tct gat gga ctg ggc       871
Leu Ser Asn Ile Gln Trp Leu Arg Lys Met Ser Ser Asp Gly Leu Gly
                185                 190                 195 tcc cgc agc atc aag caa gag atg gag gaa aag gag aat tgt cac ctg       919
Ser Arg Ser Ile Lys Gln Glu Met Glu Glu Lys Glu Asn Cys His Leu
             200                 205                 210 gag cag cga cag gtt aag gtt gag gag cct tcg aga cca tca gcg tcc       967
Glu Gln Arg Gln Val Lys Val Glu Glu Pro Ser Arg Pro Ser Ala Ser
         215                 220                 225 tgg cag aac tct gtg tct gag cgg cca ccc tac tct tac atg gcc atg      1015
Trp Gln Asn Ser Val Ser Glu Arg Pro Pro Tyr Ser Tyr Met Ala Met
 230                 235                 240 ata caa ttc gcc atc aac agc act gag agg aag cgc atg act ttg aaa      1063
Ile Gln Phe Ala Ile Asn Ser Thr Glu Arg Lys Arg Met Thr Leu Lys
245                 250                 255                 260 gac atc tat acg tgg att gag gac cac ttt ccc tac ttt aag cac att      1111
Asp Ile Tyr Thr Trp Ile Glu Asp His Phe Pro Tyr Phe Lys His Ile
                265                 270                 275
```

```
gcc aag cca ggc tgg aag aac tcc atc cgc cac aac ctt tcc ctg cac    1159
Ala Lys Pro Gly Trp Lys Asn Ser Ile Arg His Asn Leu Ser Leu His
        280                 285                 290 gac atg ttt gtc cgg gag acg tct gcc aat ggc aag gtc tcc ttc tgg    1207
Asp Met Phe Val Arg Glu Thr Ser Ala Asn Gly Lys Val Ser Phe Trp
    295                 300                 305 acc att cac ccc agt gcc aac cgc tac ttg aca ttg gac cag gtg ttt    1255
Thr Ile His Pro Ser Ala Asn Arg Tyr Leu Thr Leu Asp Gln Val Phe
310                 315                 320 aag cca ctg gac cca ggg tct cca caa ttg ccc gag cac ttg gaa tca    1303
Lys Pro Leu Asp Pro Gly Ser Pro Gln Leu Pro Glu His Leu Glu Ser
325                 330                 335                 340 cag cag aaa cga ccg aat cca gag ctc cgc cgg aac atg acc atc aaa    1351
Gln Gln Lys Arg Pro Asn Pro Glu Leu Arg Arg Asn Met Thr Ile Lys
                345                 350                 355 acc gaa ctc ccc ctg ggc gca cgg cgg aag atg aag cca ctg cta cca    1399
Thr Glu Leu Pro Leu Gly Ala Arg Arg Lys Met Lys Pro Leu Leu Pro
            360                 365                 370 cgg gtc agc tca tac ctg gta cct atc cag ttc ccg gtg aac cag tca    1447
Arg Val Ser Ser Tyr Leu Val Pro Ile Gln Phe Pro Val Asn Gln Ser
        375                 380                 385 ctg gtg ttg cag ccc tcg gtg aag gtg cca ttg ccc ctg gcg gct tcc    1495
Leu Val Leu Gln Pro Ser Val Lys Val Pro Leu Pro Leu Ala Ala Ser
    390                 395                 400 ctc atg agc tca gag ctt gcc cgc cat agc aag cga gtc cgc att gcc    1543
Leu Met Ser Ser Glu Leu Ala Arg His Ser Lys Arg Val Arg Ile Ala
405                 410                 415                 420 ccc aag gtt ttt ggg gaa cag gtg gtg ttt ggt tac atg agt aag ttc    1591
Pro Lys Val Phe Gly Glu Gln Val Val Phe Gly Tyr Met Ser Lys Phe
                425                 430                 435 ttt agt ggc gat ctg cga gat ttt ggt aca ccc atc acc agc ttg ttt    1639
Phe Ser Gly Asp Leu Arg Asp Phe Gly Thr Pro Ile Thr Ser Leu Phe
            440                 445                 450 aat ttt atc ttt ctt tgt tta tca gtg ctg cta gct gag gag ggg ata    1687
Asn Phe Ile Phe Leu Cys Leu Ser Val Leu Leu Ala Glu Glu Gly Ile
        455                 460                 465 gct cct ctt tct tct gca gga cca ggg aaa gag gag aaa ctc ctg ttt    1735
Ala Pro Leu Ser Ser Ala Gly Pro Gly Lys Glu Glu Lys Leu Leu Phe
    470                 475                 480 gga gaa ggg ttt tct cct ttg ctt cca gtt cag act atc aag gag gaa    1783
Gly Glu Gly Phe Ser Pro Leu Leu Pro Val Gln Thr Ile Lys Glu Glu
485                 490                 495                 500 gaa atc cag cct ggg gag gaa atg cca cac tta gcg aga ccc atc aaa    1831
Glu Ile Gln Pro Gly Glu Glu Met Pro His Leu Ala Arg Pro Ile Lys
                505                 510                 515 gtg gag agc cct ccc ttg gaa gag tgg ccc tcc ccg gcc cca tct ttc    1879
Val Glu Ser Pro Pro Leu Glu Glu Trp Pro Ser Pro Ala Pro Ser Phe
            520                 525                 530 aaa gag gaa tca tct cac tcc tgg gag gat tcg tcc caa tct ccc acc    1927
Lys Glu Glu Ser Ser His Ser Trp Glu Asp Ser Ser Gln Ser Pro Thr
        535                 540                 545 cca aga ccc aag aag tcc tac agt ggg ctt agg tcc cca acc cgg tgt    1975
Pro Arg Pro Lys Lys Ser Tyr Ser Gly Leu Arg Ser Pro Thr Arg Cys
    550                 555                 560 gtc tcg gaa atg ctt gtg att caa cac agg gag agg agg gag agg agc    2023
Val Ser Glu Met Leu Val Ile Gln His Arg Glu Arg Arg Glu Arg Ser
565                 570                 575                 580 cgg tct cgg agg aaa cag cat cta ctg cct ccc tgt gtg gat gag ccg    2071
Arg Ser Arg Arg Lys Gln His Leu Leu Pro Pro Cys Val Asp Glu Pro
```

|   |   |   |   |   |   |   |   |   |   |   |   |   |   |   |   |
|---|---|---|---|---|---|---|---|---|---|---|---|---|---|---|---|
|   |   | 585 |   |   |   | 590 |   |   |   | 595 |   |   |   |   |   |
| gag | ctg | ctc | ttc | tca | gag | ggg | ccc | agt | act | tcc | cgc | tgg | gcc | gca | gag |
| Glu | Leu | Leu | Phe | Ser | Glu | Gly | Pro | Ser | Thr | Ser | Arg | Trp | Ala | Ala | Glu |
|   |   | 600 |   |   |   | 605 |   |   |   | 610 |   |   |   |   | 2119 |

| ctc | ccg | ttc | cca | gca | gac | tcc | tct | gac | cct | gcc | tcc | cag | ctc | agc | tac |
|---|---|---|---|---|---|---|---|---|---|---|---|---|---|---|---|
| Leu | Pro | Phe | Pro | Ala | Asp | Ser | Ser | Asp | Pro | Ala | Ser | Gln | Leu | Ser | Tyr |
|   | 615 |   |   |   | 620 |   |   |   | 625 |   |   |   |   |   | 2167 |

| tcc | cag | gaa | gtg | gga | gga | cct | ttt | aag | aca | ccc | att | aag | gaa | acg | ctg |
|---|---|---|---|---|---|---|---|---|---|---|---|---|---|---|---|
| Ser | Gln | Glu | Val | Gly | Gly | Pro | Phe | Lys | Thr | Pro | Ile | Lys | Glu | Thr | Leu |
|   | 630 |   |   |   | 635 |   |   |   | 640 |   |   |   |   |   | 2215 |

| ccc | atc | tcc | tcc | acc | ccg | agc | aaa | tct | gtc | ctc | ccc | aga | acc | cct | gaa |
|---|---|---|---|---|---|---|---|---|---|---|---|---|---|---|---|
| Pro | Ile | Ser | Ser | Thr | Pro | Ser | Lys | Ser | Val | Leu | Pro | Arg | Thr | Pro | Glu |
| 645 |   |   |   | 650 |   |   |   | 655 |   |   |   | 660 |   |   | 2263 |

| tcc | tgg | agg | ctc | acg | ccc | cca | gcc | aaa | gta | ggg | gga | ctg | gat | ttc | agc |
|---|---|---|---|---|---|---|---|---|---|---|---|---|---|---|---|
| Ser | Trp | Arg | Leu | Thr | Pro | Pro | Ala | Lys | Val | Gly | Gly | Leu | Asp | Phe | Ser |
|   |   |   | 665 |   |   |   | 670 |   |   |   | 675 |   |   |   | 2311 |

| cca | gta | caa | acc | tcc | cag | ggt | gcc | tct | gac | ccc | ttg | cct | gac | ccc | ctg |
|---|---|---|---|---|---|---|---|---|---|---|---|---|---|---|---|
| Pro | Val | Gln | Thr | Ser | Gln | Gly | Ala | Ser | Asp | Pro | Leu | Pro | Asp | Pro | Leu |
|   |   | 680 |   |   |   | 685 |   |   |   | 690 |   |   |   |   | 2359 |

| ggg | ctg | atg | gat | ctc | agc | acc | act | ccc | ttg | caa | agt | gct | ccc | ccc | ctt |
|---|---|---|---|---|---|---|---|---|---|---|---|---|---|---|---|
| Gly | Leu | Met | Asp | Leu | Ser | Thr | Thr | Pro | Leu | Gln | Ser | Ala | Pro | Pro | Leu |
|   | 695 |   |   |   | 700 |   |   |   | 705 |   |   |   |   |   | 2407 |

| gaa | tca | ccg | caa | agg | ctc | ctc | agt | tca | gaa | ccc | tta | gac | ctc | atc | tcc |
|---|---|---|---|---|---|---|---|---|---|---|---|---|---|---|---|
| Glu | Ser | Pro | Gln | Arg | Leu | Leu | Ser | Ser | Glu | Pro | Leu | Asp | Leu | Ile | Ser |
| 710 |   |   |   | 715 |   |   |   | 720 |   |   |   |   |   |   | 2455 |

| gtc | ccc | ttt | ggc | aac | tct | tct | ccc | tca | gat | ata | gac | gtc | ccc | aag | cca |
|---|---|---|---|---|---|---|---|---|---|---|---|---|---|---|---|
| Val | Pro | Phe | Gly | Asn | Ser | Ser | Pro | Ser | Asp | Ile | Asp | Val | Pro | Lys | Pro |
| 725 |   |   |   | 730 |   |   |   | 735 |   |   |   | 740 |   |   | 2503 |

| ggc | tcc | ccg | gag | cca | cag | gtt | tct | ggc | ctt | gca | gcc | aat | cgt | tct | ctg |
|---|---|---|---|---|---|---|---|---|---|---|---|---|---|---|---|
| Gly | Ser | Pro | Glu | Pro | Gln | Val | Ser | Gly | Leu | Ala | Ala | Asn | Arg | Ser | Leu |
|   |   |   | 745 |   |   |   | 750 |   |   |   | 755 |   |   |   | 2551 |

| aca | gaa | ggc | ctg | gtc | ctg | gac | aca | atg | aat | gac | agc | ctc | agc | aag | atc |
|---|---|---|---|---|---|---|---|---|---|---|---|---|---|---|---|
| Thr | Glu | Gly | Leu | Val | Leu | Asp | Thr | Met | Asn | Asp | Ser | Leu | Ser | Lys | Ile |
|   |   | 760 |   |   |   | 765 |   |   |   | 770 |   |   |   |   | 2599 |

| ctg | ctg | gac | atc | agc | ttt | cct | ggc | ctg | gac | gag | gac | cca | ctg | ggc | cct |
|---|---|---|---|---|---|---|---|---|---|---|---|---|---|---|---|
| Leu | Leu | Asp | Ile | Ser | Phe | Pro | Gly | Leu | Asp | Glu | Asp | Pro | Leu | Gly | Pro |
|   | 775 |   |   |   | 780 |   |   |   | 785 |   |   |   |   |   | 2647 |

| gac | aac | atc | aac | tgg | tcc | cag | ttt | att | cct | gag | cta | cag | tag |   |   |
|---|---|---|---|---|---|---|---|---|---|---|---|---|---|---|---|
| Asp | Asn | Ile | Asn | Trp | Ser | Gln | Phe | Ile | Pro | Glu | Leu | Gln |   |   |   |
| 790 |   |   |   | 795 |   |   |   | 800 |   |   |   |   |   |   | 2689 |

| agccctgccc | ttgcccctgt | gctcaagctg | tccaccatcc | cgggcactcc | aaggctcagt | 2749 |
|---|---|---|---|---|---|---|
| gcacccaag | cctctgagtg | aggacagcag | gcagggactg | ttctgctcct | catagctccc | 2809 |
| tgctgcctga | ttatgcaaaa | gtagcagtca | caccctagcc | actgctggga | ccttgtgttc | 2869 |
| cccaagagta | tctgattcct | ctgctgtccc | tgccaggagc | tgaagggtgg | gaacaacaaa | 2929 |
| ggcaatggtg | aaaagagatt | aggaaccccc | cagcctgttt | ccattctctg | cccagcagtc | 2989 |
| tcttaccttc | cctgatcttt | gcagggtggt | ccgtgtaaat | agtataaatt | ctccaaatta | 3049 |
| tcctctaatt | ataaatgtaa | gcttatttcc | ttagatcatt | atccagagac | tgccagaagg | 3109 |
| tgggtaggat | gacctggggg | ttcaattgac | ttctgttcct | tgcttttagt | tttgatagaa | 3169 |
| gggaagacct | gcagtgcacg | gtttcttcca | ggctgaggta | cctggatctt | gggttcttca | 3229 |
| ctgcagggac | ccagacaagt | ggatctgctt | gccagagtcc | tttttgcccc | tccctgccac | 3289 |
| ctccccgtgt | ttccaagtca | gctttcctgc | aagaagaaat | cctggttaaa | aaagtctttt | 3349 |
| gtattgggtc | aggagttgaa | tttggggtgg | gaggatggat | gcaactgaag | cagagtgtgg | 3409 |
| gtgcccagat | gtgcgctatt | agatgtttct | ctgataatgt | ccccaatcat | accagggaga | 3469 |

```
ctggcattga cgagaactca ggtggaggct tgagaaggcc gaaagggccc ctgacctgcc   3529
tggcttcctt agcttgcccc tcagctttgc aaagagccac cctaggcccc agctgaccgc   3589
atgggtgtga gccagcttga gaacactaac tactcaataa aagcgaaggt ggacatgaaa   3649
aaaaaaaaaa aaaaa                                                    3665

<210> SEQ ID NO 5
<211> LENGTH: 801
<212> TYPE: PRT
<213> ORGANISM: Homo sapiens

<400> SEQUENCE: 5
```

Met Lys Thr Ser Pro Arg Arg Pro Leu Ile Leu Lys Arg Arg Leu
1               5                   10                  15

Pro Leu Pro Val Gln Asn Ala Pro Ser Glu Thr Ser Glu Glu Pro
            20                  25                  30

Lys Arg Ser Pro Ala Gln Gln Glu Ser Asn Gln Ala Glu Ala Ser Lys
            35                  40                  45

Glu Val Ala Glu Ser Asn Ser Cys Lys Phe Pro Ala Gly Ile Lys Ile
    50                  55                  60

Ile Asn His Pro Thr Met Pro Asn Thr Gln Val Val Ala Ile Pro Asn
65                  70                  75                  80

Asn Ala Asn Ile His Ser Ile Ile Thr Ala Leu Thr Ala Lys Gly Lys
                85                  90                  95

Glu Ser Gly Ser Ser Gly Pro Asn Lys Phe Ile Leu Ile Ser Cys Gly
            100                 105                 110

Gly Ala Pro Thr Gln Pro Pro Gly Leu Arg Pro Gln Thr Gln Thr Ser
            115                 120                 125

Tyr Asp Ala Lys Arg Thr Glu Val Thr Leu Glu Thr Leu Gly Pro Lys
    130                 135                 140

Pro Ala Ala Arg Asp Val Asn Leu Pro Arg Pro Pro Gly Ala Leu Cys
145                 150                 155                 160

Glu Gln Lys Arg Glu Thr Cys Ala Asp Gly Glu Ala Ala Gly Cys Thr
                165                 170                 175

Ile Asn Asn Ser Leu Ser Asn Ile Gln Trp Leu Arg Lys Met Ser Ser
            180                 185                 190

Asp Gly Leu Gly Ser Arg Ser Ile Lys Gln Glu Met Glu Glu Lys Glu
            195                 200                 205

Asn Cys His Leu Glu Gln Arg Gln Val Lys Val Glu Glu Pro Ser Arg
    210                 215                 220

Pro Ser Ala Ser Trp Gln Asn Ser Val Ser Glu Arg Pro Pro Tyr Ser
225                 230                 235                 240

Tyr Met Ala Met Ile Gln Phe Ala Ile Asn Ser Thr Glu Arg Lys Arg
                245                 250                 255

Met Thr Leu Lys Asp Ile Tyr Thr Trp Ile Glu Asp His Phe Pro Tyr
            260                 265                 270

Phe Lys His Ile Ala Lys Pro Gly Trp Lys Asn Ser Ile Arg His Asn
    275                 280                 285

Leu Ser Leu His Asp Met Phe Val Arg Glu Thr Ser Ala Asn Gly Lys
    290                 295                 300

Val Ser Phe Trp Thr Ile His Pro Ser Ala Asn Arg Tyr Leu Thr Leu
305                 310                 315                 320

Asp Gln Val Phe Lys Pro Leu Asp Pro Gly Ser Pro Gln Leu Pro Glu
                325                 330                 335

```
His Leu Glu Ser Gln Gln Lys Arg Pro Asn Pro Glu Leu Arg Arg Asn
            340                 345                 350

Met Thr Ile Lys Thr Glu Leu Pro Leu Gly Ala Arg Arg Lys Met Lys
            355                 360                 365

Pro Leu Leu Pro Arg Val Ser Ser Tyr Leu Val Pro Ile Gln Phe Pro
            370                 375                 380

Val Asn Gln Ser Leu Val Leu Gln Pro Ser Val Lys Val Pro Leu Pro
385                 390                 395                 400

Leu Ala Ala Ser Leu Met Ser Ser Glu Leu Ala Arg His Ser Lys Arg
                405                 410                 415

Val Arg Ile Ala Pro Lys Val Phe Gly Glu Gln Val Val Phe Gly Tyr
            420                 425                 430

Met Ser Lys Phe Phe Ser Gly Asp Leu Arg Asp Phe Gly Thr Pro Ile
            435                 440                 445

Thr Ser Leu Phe Asn Phe Ile Phe Leu Cys Leu Ser Val Leu Leu Ala
            450                 455                 460

Glu Glu Gly Ile Ala Pro Leu Ser Ser Ala Gly Pro Gly Lys Glu Glu
465                 470                 475                 480

Lys Leu Leu Phe Gly Glu Gly Phe Ser Pro Leu Leu Pro Val Gln Thr
                485                 490                 495

Ile Lys Glu Glu Glu Ile Gln Pro Gly Glu Glu Met Pro His Leu Ala
            500                 505                 510

Arg Pro Ile Lys Val Glu Ser Pro Pro Leu Glu Glu Trp Pro Ser Pro
            515                 520                 525

Ala Pro Ser Phe Lys Glu Ser Ser His Ser Trp Glu Asp Ser Ser
            530                 535                 540

Gln Ser Pro Thr Pro Arg Pro Lys Lys Ser Tyr Ser Gly Leu Arg Ser
545                 550                 555                 560

Pro Thr Arg Cys Val Ser Glu Met Leu Val Ile Gln His Arg Glu Arg
                565                 570                 575

Arg Glu Arg Ser Arg Ser Arg Arg Lys Gln His Leu Leu Pro Pro Cys
            580                 585                 590

Val Asp Glu Pro Glu Leu Leu Phe Ser Glu Gly Pro Ser Thr Ser Arg
            595                 600                 605

Trp Ala Ala Glu Leu Pro Phe Pro Ala Asp Ser Ser Asp Pro Ala Ser
            610                 615                 620

Gln Leu Ser Tyr Ser Gln Glu Val Gly Gly Pro Phe Lys Thr Pro Ile
625                 630                 635                 640

Lys Glu Thr Leu Pro Ile Ser Ser Thr Pro Ser Lys Ser Val Leu Pro
                645                 650                 655

Arg Thr Pro Glu Ser Trp Arg Leu Thr Pro Ala Lys Val Gly Gly
            660                 665                 670

Leu Asp Phe Ser Pro Val Gln Thr Ser Gln Gly Ala Ser Asp Pro Leu
            675                 680                 685

Pro Asp Pro Leu Gly Leu Met Asp Leu Ser Thr Thr Pro Leu Gln Ser
            690                 695                 700

Ala Pro Pro Leu Glu Ser Pro Gln Arg Leu Leu Ser Ser Glu Pro Leu
705                 710                 715                 720

Asp Leu Ile Ser Val Pro Phe Gly Asn Ser Ser Pro Ser Asp Ile Asp
                725                 730                 735

Val Pro Lys Pro Gly Ser Pro Glu Pro Gln Val Ser Gly Leu Ala Ala
            740                 745                 750
```

```
Asn Arg Ser Leu Thr Glu Gly Leu Val Leu Asp Thr Met Asn Asp Ser
        755                 760                 765

Leu Ser Lys Ile Leu Leu Asp Ile Ser Phe Pro Gly Leu Asp Glu Asp
    770                 775                 780

Pro Leu Gly Pro Asp Asn Ile Asn Trp Ser Gln Phe Ile Pro Glu Leu
785                 790                 795                 800

Gln

<210> SEQ ID NO 6
<211> LENGTH: 3506
<212> TYPE: DNA
<213> ORGANISM: Homo sapiens
<220> FEATURE:
<221> NAME/KEY: CDS
<222> LOCATION: (284)..(2530)

<400> SEQUENCE: 6
tttcaaacag cggaacaaac tgaaagctcc ggtgccagac cccaccccg gccccggccc      60 gggaccccct ccctcccgg atccccggg ggttcccacc ccgcccgcac cgccggggac     120
ccggccggtc cggcgcgagc ccccgtccgg ggccctggct cggccccag gttggaggag     180 cccgagcccc gccttcggag ctacggccta acggcggcgg cgactgcagt ctggagggtc     240
cacacttgtg attctcaatg gagagtgaaa acgcagattc ata atg aaa act agc     295
                                               Met Lys Thr Ser
                                                 1 ccc cgt cgg cca ctg att ctc aaa aga cgg agg ctg ccc ctt cct gtt     343
Pro Arg Arg Pro Leu Ile Leu Lys Arg Arg Arg Leu Pro Leu Pro Val
  5              10                  15                  20 caa aat gcc cca agt gaa aca tca gag gag gaa cct aag aga tcc cct     391
Gln Asn Ala Pro Ser Glu Thr Ser Glu Glu Glu Pro Lys Arg Ser Pro
                 25                  30                  35 gcc caa cag gag tct aat caa gca gag gcc tcc aag gaa gtg gca gag     439
Ala Gln Gln Glu Ser Asn Gln Ala Glu Ala Ser Lys Glu Val Ala Glu
         40                  45                  50 tcc aac tct tgc aag ttt cca gct ggg atc aag att att aac cac ccc     487
Ser Asn Ser Cys Lys Phe Pro Ala Gly Ile Lys Ile Ile Asn His Pro
     55                  60                  65 acc atg ccc aac acg caa gta gtg gcc atc ccc aac aat gct aat att     535
Thr Met Pro Asn Thr Gln Val Val Ala Ile Pro Asn Asn Ala Asn Ile
 70                  75                  80 cac agc atc atc aca gca ctg act gcc aag gga aaa gag agt ggc agt     583
His Ser Ile Ile Thr Ala Leu Thr Ala Lys Gly Lys Glu Ser Gly Ser
85                  90                  95                 100 agt ggg ccc aac aaa ttc atc ctc atc agc tgt ggg gga gcc cca act     631
Ser Gly Pro Asn Lys Phe Ile Leu Ile Ser Cys Gly Gly Ala Pro Thr
                105                 110                 115 cag cct cca gga ctc cgg cct caa acc caa acc agc tat gat gcc aaa     679
Gln Pro Pro Gly Leu Arg Pro Gln Thr Gln Thr Ser Tyr Asp Ala Lys
            120                 125                 130 agg aca gaa gtg acc ctg gag acc ttg gga cca aaa cct gca gct agg     727
Arg Thr Glu Val Thr Leu Glu Thr Leu Gly Pro Lys Pro Ala Ala Arg
        135                 140                 145 gat gtg aat ctt cct aga cca cct gga gcc ctt tgc gag cag aaa cgg     775
Asp Val Asn Leu Pro Arg Pro Pro Gly Ala Leu Cys Glu Gln Lys Arg
    150                 155                 160 gag acc tgt gca gat ggt gag gca gca ggc tgc act atc aac aat agc     823
Glu Thr Cys Ala Asp Gly Glu Ala Ala Gly Cys Thr Ile Asn Asn Ser
165                 170                 175                 180 cta tcc aac atc cag tgg ctt cga aag atg agt tct gat gga ctg ggc     871
```

|     |     |     |     |     |     |     |     |     |     |     |     |     |     |
| --- | --- | --- | --- | --- | --- | --- | --- | --- | --- | --- | --- | --- | --- |
| Leu | Ser | Asn | Ile | Gln | Trp | Leu | Arg | Lys | Met | Ser | Ser | Asp | Gly | Leu | Gly |
|     |     |     |     | 185 |     |     |     | 190 |     |     |     | 195 |     |

```
tcc cgc agc atc aag caa gag atg gag gaa aag gag aat tgt cac ctg   919
Ser Arg Ser Ile Lys Gln Glu Met Glu Glu Lys Glu Asn Cys His Leu
        200                 205                 210 gag cag cga cag gtt aag gtt gag gag cct tcg aga cca tca gcg tcc   967
Glu Gln Arg Gln Val Lys Val Glu Glu Pro Ser Arg Pro Ser Ala Ser
            215                 220                 225 tgg cag aac tct gtg tct gag cgg cca ccc tac tct tac atg gcc atg  1015
Trp Gln Asn Ser Val Ser Glu Arg Pro Pro Tyr Ser Tyr Met Ala Met
        230                 235                 240 ata caa ttc gcc atc aac agc act gag agg aag cgc atg act ttg aaa  1063
Ile Gln Phe Ala Ile Asn Ser Thr Glu Arg Lys Arg Met Thr Leu Lys
245                 250                 255                 260 gac atc tat acg tgg att gag gac cac ttt ccc tac ttt aag cac att  1111
Asp Ile Tyr Thr Trp Ile Glu Asp His Phe Pro Tyr Phe Lys His Ile
                265                 270                 275 gcc aag cca ggc tgg aag aac tcc atc cgc cac aac ctt tcc ctg cac  1159
Ala Lys Pro Gly Trp Lys Asn Ser Ile Arg His Asn Leu Ser Leu His
            280                 285                 290 gac atg ttt gtc cgg gag acg tct gcc aat ggc aag gtc tcc ttc tgg  1207
Asp Met Phe Val Arg Glu Thr Ser Ala Asn Gly Lys Val Ser Phe Trp
        295                 300                 305 acc att cac ccc agt gcc aac cgc tac ttg aca ttg gac cag gtg ttt  1255
Thr Ile His Pro Ser Ala Asn Arg Tyr Leu Thr Leu Asp Gln Val Phe
310                 315                 320 aag cag cag aaa cga ccg aat cca gag ctc cgc cgg aac atg acc atc  1303
Lys Gln Gln Lys Arg Pro Asn Pro Glu Leu Arg Arg Asn Met Thr Ile
325                 330                 335                 340 aaa acc gaa ctc ccc ctg ggc gca cgg cgg aag atg aag cca ctg cta  1351
Lys Thr Glu Leu Pro Leu Gly Ala Arg Arg Lys Met Lys Pro Leu Leu
                345                 350                 355 cca cgg gtc agc tca tac ctg gta cct atc cag ttc ccg gtg aac cag  1399
Pro Arg Val Ser Ser Tyr Leu Val Pro Ile Gln Phe Pro Val Asn Gln
            360                 365                 370 tca ctg gtg ttg cag ccc tcg gtg aag gtg cca ttg ccc ctg gcg gct  1447
Ser Leu Val Leu Gln Pro Ser Val Lys Val Pro Leu Pro Leu Ala Ala
        375                 380                 385 tcc ctc atg agc tca gag ctt gcc cgc cat agc aag cga gtc cgc att  1495
Ser Leu Met Ser Ser Glu Leu Ala Arg His Ser Lys Arg Val Arg Ile
390                 395                 400 gcc ccc aag gtg ctg cta gct gag gag ggg ata gct cct ctt tct tct  1543
Ala Pro Lys Val Leu Leu Ala Glu Glu Gly Ile Ala Pro Leu Ser Ser
405                 410                 415                 420 gca gga cca ggg aaa gag gag aaa ctc ctg ttt gga gaa ggg ttt tct  1591
Ala Gly Pro Gly Lys Glu Glu Lys Leu Leu Phe Gly Glu Gly Phe Ser
                425                 430                 435 cct ttg ctt cca gtt cag act atc aag gag gaa gaa atc cag cct ggg  1639
Pro Leu Leu Pro Val Gln Thr Ile Lys Glu Glu Glu Ile Gln Pro Gly
            440                 445                 450 gag gaa atg cca cac tta gcg aga ccc atc aaa gtg gag agc cct ccc  1687
Glu Glu Met Pro His Leu Ala Arg Pro Ile Lys Val Glu Ser Pro Pro
        455                 460                 465 ttg gaa gag tgg ccc tcc ccg gcc cca tct ttc aaa gag gaa tca tct  1735
Leu Glu Glu Trp Pro Ser Pro Ala Pro Ser Phe Lys Glu Glu Ser Ser
470                 475                 480 cac tcc tgg gag gat tcg tcc caa tct ccc acc cca aga ccc aag aag  1783
His Ser Trp Glu Asp Ser Ser Gln Ser Pro Thr Pro Arg Pro Lys Lys
485                 490                 495                 500
```

| | | |
|---|---|---|
| tcc tac agt ggg ctt agg tcc cca acc cgg tgt gtc tcg gaa atg ctt<br>Ser Tyr Ser Gly Leu Arg Ser Pro Thr Arg Cys Val Ser Glu Met Leu<br>                    505                     510                  515 | 1831 |
| gtg att caa cac agg gag agg agg gag agg agc cgg tct cgg agg aaa<br>Val Ile Gln His Arg Glu Arg Arg Glu Arg Ser Arg Ser Arg Arg Lys<br>520                   525                   530 | 1879 |
| cag cat cta ctg cct ccc tgt gtg gat gag ccg gag ctg ctc ttc tca<br>Gln His Leu Leu Pro Pro Cys Val Asp Glu Pro Glu Leu Leu Phe Ser<br>        535                    540                  545 | 1927 |
| gag ggg ccc agt act tcc cgc tgg gcc gca gag ctc ccg ttc cca gca<br>Glu Gly Pro Ser Thr Ser Arg Trp Ala Ala Glu Leu Pro Phe Pro Ala<br>550                 555                   560 | 1975 |
| gac tcc tct gac cct gcc tcc cag ctc agc tac tcc cag gaa gtg gga<br>Asp Ser Ser Asp Pro Ala Ser Gln Leu Ser Tyr Ser Gln Glu Val Gly<br>565                  570                 575                580 | 2023 |
| gga cct ttt aag aca ccc att aag gaa acg ctg ccc atc tcc tcc acc<br>Gly Pro Phe Lys Thr Pro Ile Lys Glu Thr Leu Pro Ile Ser Ser Thr<br>                 585                   590                 595 | 2071 |
| ccg agc aaa tct gtc ctc ccc aga acc cct gaa tcc tgg agg ctc acg<br>Pro Ser Lys Ser Val Leu Pro Arg Thr Pro Glu Ser Trp Arg Leu Thr<br>600                 605                   610 | 2119 |
| ccc cca gcc aaa gta ggg gga ctg gat ttc agc cca gta caa acc tcc<br>Pro Pro Ala Lys Val Gly Gly Leu Asp Phe Ser Pro Val Gln Thr Ser<br>        615                    620                  625 | 2167 |
| cag ggt gcc tct gac ccc ttg cct gac ccc ctg ggg ctg atg gat ctc<br>Gln Gly Ala Ser Asp Pro Leu Pro Asp Pro Leu Gly Leu Met Asp Leu<br>630                 635                   640 | 2215 |
| agc acc act ccc ttg caa agt gct ccc ccc ctt gaa tca ccg caa agg<br>Ser Thr Thr Pro Leu Gln Ser Ala Pro Pro Leu Glu Ser Pro Gln Arg<br>645                 650                   655                660 | 2263 |
| ctc ctc agt tca gaa ccc tta gac ctc atc tcc gtc ccc ttt ggc aac<br>Leu Leu Ser Ser Glu Pro Leu Asp Leu Ile Ser Val Pro Phe Gly Asn<br>               665                   670                  675 | 2311 |
| tct tct ccc tca gat ata gac gtc ccc aag cca ggc tcc ccg gag cca<br>Ser Ser Pro Ser Asp Ile Asp Val Pro Lys Pro Gly Ser Pro Glu Pro<br>        680                    685                  690 | 2359 |
| cag gtt tct ggc ctt gca gcc aat cgt tct ctg aca gaa ggc ctg gtc<br>Gln Val Ser Gly Leu Ala Ala Asn Arg Ser Leu Thr Glu Gly Leu Val<br>695                 700                   705 | 2407 |
| ctg gac aca atg aat gac agc ctc agc aag atc ctg ctg gac atc agc<br>Leu Asp Thr Met Asn Asp Ser Leu Ser Lys Ile Leu Leu Asp Ile Ser<br>        710                    715                  720 | 2455 |
| ttt cct ggc ctg gac gag gac cca ctg ggc cct gac aac atc aac tgg<br>Phe Pro Gly Leu Asp Glu Asp Pro Leu Gly Pro Asp Asn Ile Asn Trp<br>725                 730                   735                740 | 2503 |
| tcc cag ttt att cct gag cta cag tag agccctgccc ttgccctgt<br>Ser Gln Phe Ile Pro Glu Leu Gln<br>               745 | 2550 |
| gctcaagctg tccaccatcc cgggcactcc aaggctcagt gcaccccaag cctctgagtg | 2610 |
| aggacagcag gcagggactg ttctgctcct catagctccc tgctgcctga ttatgcaaaa | 2670 |
| gtagcagtca caccctagcc actgctggga ccttgtgttc cccaagagta tctgattcct | 2730 |
| ctgctgtccc tgccaggagc tgaagggtgg gaacaacaaa ggcaatggtg aaaagagatt | 2790 |
| aggaaccccc cagcctgttt ccattctctg cccagcagtc tcttaccttc cctgatcttt | 2850 |
| gcagggtggt ccgtgtaaat agtataaatt ctccaaatta tcctctaatt ataaatgtaa | 2910 |
| gcttatttcc ttagatcatt atccagagac tgccagaagg tgggtaggat gacctggggt | 2970 |
| ttcaattgac ttctgttcct tgcttttagt tttgatagaa gggaagacct gcagtgcacg | 3030 |

-continued

```
gtttcttcca ggctgaggta cctggatctt gggttcttca ctgcagggac ccagacaagt    3090
ggatctgctt gccagagtcc tttttgcccc tccctgccac ctccccgtgt ttccaagtca    3150
gctttcctgc aagaagaaat cctggttaaa aaagtctttt gtattgggtc aggagttgaa    3210
tttggggtgg gaggatggat gcaactgaag cagagtgtgg gtgcccagat gtgcgctatt    3270
agatgtttct ctgataatgt ccccaatcat accagggaga ctggcattga cgagaactca    3330
ggtggaggct tgagaaggcc gaaagggccc ctgacctgcc tggcttcctt agcttgcccc    3390
tcagctttgc aaagagccac cctaggcccc agctgaccgc atgggtgtga gccagcttga    3450
gaacactaac tactcaataa aagcgaaggt ggacatgaaa aaaaaaaaa aaaaaa         3506
```

<210> SEQ ID NO 7
<211> LENGTH: 748
<212> TYPE: PRT
<213> ORGANISM: Homo sapiens

<400> SEQUENCE: 7

```
Met Lys Thr Ser Pro Arg Arg Pro Leu Ile Leu Lys Arg Arg Arg Leu
1               5                   10                  15

Pro Leu Pro Val Gln Asn Ala Pro Ser Glu Thr Ser Glu Glu Glu Pro
            20                  25                  30

Lys Arg Ser Pro Ala Gln Gln Glu Ser Asn Gln Ala Glu Ala Ser Lys
        35                  40                  45

Glu Val Ala Glu Ser Asn Ser Cys Lys Phe Pro Ala Gly Ile Lys Ile
    50                  55                  60

Ile Asn His Pro Thr Met Pro Asn Thr Gln Val Ala Ile Pro Asn
65                  70                  75                  80

Asn Ala Asn Ile His Ser Ile Ile Thr Ala Leu Thr Ala Lys Gly Lys
                85                  90                  95

Glu Ser Gly Ser Ser Gly Pro Asn Lys Phe Ile Leu Ile Ser Cys Gly
            100                 105                 110

Gly Ala Pro Thr Gln Pro Pro Gly Leu Arg Pro Gln Thr Gln Thr Ser
        115                 120                 125

Tyr Asp Ala Lys Arg Thr Glu Val Thr Leu Glu Thr Leu Gly Pro Lys
    130                 135                 140

Pro Ala Ala Arg Asp Val Asn Leu Pro Arg Pro Pro Gly Ala Leu Cys
145                 150                 155                 160

Glu Gln Lys Arg Glu Thr Cys Ala Asp Gly Glu Ala Ala Gly Cys Thr
                165                 170                 175

Ile Asn Asn Ser Leu Ser Asn Ile Gln Trp Leu Arg Lys Met Ser Ser
            180                 185                 190

Asp Gly Leu Gly Ser Arg Ser Ile Lys Gln Glu Met Glu Glu Lys Glu
        195                 200                 205

Asn Cys His Leu Glu Gln Arg Gln Val Lys Val Glu Glu Pro Ser Arg
    210                 215                 220

Pro Ser Ala Ser Trp Gln Asn Ser Val Ser Glu Arg Pro Pro Tyr Ser
225                 230                 235                 240

Tyr Met Ala Met Ile Gln Phe Ala Ile Asn Ser Thr Glu Arg Lys Arg
                245                 250                 255

Met Thr Leu Lys Asp Ile Tyr Thr Trp Ile Glu Asp His Phe Pro Tyr
            260                 265                 270

Phe Lys His Ile Ala Lys Pro Gly Trp Lys Asn Ser Ile Arg His Asn
        275                 280                 285
```

```
Leu Ser Leu His Asp Met Phe Val Arg Glu Thr Ser Ala Asn Gly Lys
    290                 295                 300

Val Ser Phe Trp Thr Ile His Pro Ser Ala Asn Arg Tyr Leu Thr Leu
305                 310                 315                 320

Asp Gln Val Phe Lys Gln Gln Lys Arg Pro Asn Pro Glu Leu Arg Arg
                325                 330                 335

Asn Met Thr Ile Lys Thr Glu Leu Pro Leu Gly Ala Arg Arg Lys Met
                340                 345                 350

Lys Pro Leu Leu Pro Arg Val Ser Ser Tyr Leu Val Pro Ile Gln Phe
            355                 360                 365

Pro Val Asn Gln Ser Leu Val Leu Gln Pro Ser Val Lys Val Pro Leu
370                 375                 380

Pro Leu Ala Ala Ser Leu Met Ser Ser Glu Leu Ala Arg His Ser Lys
385                 390                 395                 400

Arg Val Arg Ile Ala Pro Lys Val Leu Leu Ala Glu Glu Gly Ile Ala
                405                 410                 415

Pro Leu Ser Ser Ala Gly Pro Gly Lys Glu Lys Leu Leu Phe Gly
            420                 425                 430

Glu Gly Phe Ser Pro Leu Leu Pro Val Gln Thr Ile Lys Glu Glu Glu
            435                 440                 445

Ile Gln Pro Gly Glu Glu Met Pro His Leu Ala Arg Pro Ile Lys Val
450                 455                 460

Glu Ser Pro Pro Leu Glu Glu Trp Pro Ser Pro Ala Pro Ser Phe Lys
465                 470                 475                 480

Glu Glu Ser Ser His Ser Trp Glu Asp Ser Ser Gln Ser Pro Thr Pro
                485                 490                 495

Arg Pro Lys Lys Ser Tyr Ser Gly Leu Arg Ser Pro Thr Arg Cys Val
                500                 505                 510

Ser Glu Met Leu Val Ile Gln His Arg Glu Arg Arg Glu Arg Ser Arg
            515                 520                 525

Ser Arg Arg Lys Gln His Leu Leu Pro Pro Cys Val Asp Glu Pro Glu
530                 535                 540

Leu Leu Phe Ser Glu Gly Pro Ser Thr Ser Arg Trp Ala Ala Glu Leu
545                 550                 555                 560

Pro Phe Pro Ala Asp Ser Ser Asp Pro Ala Ser Gln Leu Ser Tyr Ser
                565                 570                 575

Gln Glu Val Gly Gly Pro Phe Lys Thr Pro Ile Lys Glu Thr Leu Pro
                580                 585                 590

Ile Ser Ser Thr Pro Ser Lys Ser Val Leu Pro Arg Thr Pro Glu Ser
            595                 600                 605

Trp Arg Leu Thr Pro Pro Ala Lys Val Gly Gly Leu Asp Phe Ser Pro
610                 615                 620

Val Gln Thr Ser Gln Gly Ala Ser Asp Pro Leu Pro Asp Pro Leu Gly
625                 630                 635                 640

Leu Met Asp Leu Ser Thr Thr Pro Leu Gln Ser Ala Pro Pro Leu Glu
                645                 650                 655

Ser Pro Gln Arg Leu Leu Ser Ser Glu Pro Leu Asp Leu Ile Ser Val
            660                 665                 670

Pro Phe Gly Asn Ser Ser Pro Ser Asp Ile Asp Val Pro Lys Pro Gly
            675                 680                 685

Ser Pro Glu Pro Gln Val Ser Gly Leu Ala Ala Asn Arg Ser Leu Thr
            690                 695                 700

Glu Gly Leu Val Leu Asp Thr Met Asn Asp Ser Leu Ser Lys Ile Leu
```

```
705               710               715               720
Leu Asp Ile Ser Phe Pro Gly Leu Asp Glu Asp Pro Leu Gly Pro Asp
                    725               730               735

Asn Ile Asn Trp Ser Gln Phe Ile Pro Glu Leu Gln
            740               745

<210> SEQ ID NO 8
<211> LENGTH: 3551
<212> TYPE: DNA
<213> ORGANISM: Homo sapiens
<220> FEATURE:
<221> NAME/KEY: CDS
<222> LOCATION: (284)..(2575)

<400> SEQUENCE: 8
tttcaaacag cggaacaaac tgaaagctcc ggtgccagac cccaccccg gccccggccc        60 gggacccct ccctcccgg atccccgg ggttcccacc ccgccgcac cgccggggac           120 ccggccggtc cggcgcgagc cccgtccgg ggccctggct cggcccccag gttggaggag       180
cccggagccc gccttcggag ctacggccta acggcggcgg cgactgcagt ctggagggtc     240
cacacttgtg attctcaatg gagagtgaaa acgcagattc ata atg aaa act agc      295
                                              Met Lys Thr Ser
                                                1 ccc cgt cgg cca ctg att ctc aaa aga cgg agg ctg ccc ctt cct gtt      343
Pro Arg Arg Pro Leu Ile Leu Lys Arg Arg Arg Leu Pro Leu Pro Val
  5                  10                  15                  20 caa aat gcc cca agt gaa aca tca gag gag gaa cct aag aga tcc cct      391
Gln Asn Ala Pro Ser Glu Thr Ser Glu Glu Glu Pro Lys Arg Ser Pro
              25                  30                  35 gcc caa cag gag tct aat caa gca gag gcc tcc aag gaa gtg gca gag      439
Ala Gln Gln Glu Ser Asn Gln Ala Glu Ala Ser Lys Glu Val Ala Glu
          40                  45                  50 tcc aac tct tgc aag ttt cca gct ggg atc aag att att aac cac ccc      487
Ser Asn Ser Cys Lys Phe Pro Ala Gly Ile Lys Ile Ile Asn His Pro
      55                  60                  65 acc atg ccc aac acg caa gta gtg gcc atc ccc aac aat gct aat att      535
Thr Met Pro Asn Thr Gln Val Val Ala Ile Pro Asn Asn Ala Asn Ile
 70                  75                  80 cac agc atc atc aca gca ctg act gcc aag gga aaa gag agt ggc agt      583
His Ser Ile Ile Thr Ala Leu Thr Ala Lys Gly Lys Glu Ser Gly Ser
85                  90                  95                 100 agt ggg ccc aac aaa ttc atc ctc atc agc tgt ggg gga gcc cca act      631
Ser Gly Pro Asn Lys Phe Ile Leu Ile Ser Cys Gly Gly Ala Pro Thr
                105                 110                 115 cag cct cca gga ctc cgg cct caa acc caa acc agc tat gat gcc aaa      679
Gln Pro Pro Gly Leu Arg Pro Gln Thr Gln Thr Ser Tyr Asp Ala Lys
            120                 125                 130 agg aca gaa gtg acc ctg gag acc ttg gga cca aaa cct gca gct agg      727
Arg Thr Glu Val Thr Leu Glu Thr Leu Gly Pro Lys Pro Ala Ala Arg
        135                 140                 145 gat gtg aat ctt cct aga cca cct gga gcc ctt tgc gag cag aaa cgg      775
Asp Val Asn Leu Pro Arg Pro Pro Gly Ala Leu Cys Glu Gln Lys Arg
    150                 155                 160 gag acc tgt gca gat ggt gag gca gca ggc tgc act atc aac aat agc      823
Glu Thr Cys Ala Asp Gly Glu Ala Ala Gly Cys Thr Ile Asn Asn Ser
165                 170                 175                 180 cta tcc aac atc cag tgg ctt cga aag atg agt tct gat gga ctg ggc      871
Leu Ser Asn Ile Gln Trp Leu Arg Lys Met Ser Ser Asp Gly Leu Gly
                185                 190                 195
```

-continued

| | |
|---|---|
| tcc cgc agc atc aag caa gag atg gag gaa aag gag aat tgt cac ctg<br>Ser Arg Ser Ile Lys Gln Glu Met Glu Glu Lys Glu Asn Cys His Leu<br>200                       205                   210 | 919 |
| gag cag cga cag gtt aag gtt gag gag cct tcg aga cca tca gcg tcc<br>Glu Gln Arg Gln Val Lys Val Glu Glu Pro Ser Arg Pro Ser Ala Ser<br>215                     220                   225 | 967 |
| tgg cag aac tct gtg tct gag cgg cca ccc tac tct tac atg gcc atg<br>Trp Gln Asn Ser Val Ser Glu Arg Pro Pro Tyr Ser Tyr Met Ala Met<br>230                     235                   240 | 1015 |
| ata caa ttc gcc atc aac agc act gag agg aag cgc atg act ttg aaa<br>Ile Gln Phe Ala Ile Asn Ser Thr Glu Arg Lys Arg Met Thr Leu Lys<br>245               250                   255                   260 | 1063 |
| gac atc tat acg tgg att gag gac cac ttt ccc tac ttt aag cac att<br>Asp Ile Tyr Thr Trp Ile Glu Asp His Phe Pro Tyr Phe Lys His Ile<br>265                     270                   275 | 1111 |
| gcc aag cca ggc tgg aag aac tcc atc cgc cac aac ctt tcc ctg cac<br>Ala Lys Pro Gly Trp Lys Asn Ser Ile Arg His Asn Leu Ser Leu His<br>280                     285                   290 | 1159 |
| gac atg ttt gtc cgg gag acg tct gcc aat ggc aag gtc tcc ttc tgg<br>Asp Met Phe Val Arg Glu Thr Ser Ala Asn Gly Lys Val Ser Phe Trp<br>295                     300                   305 | 1207 |
| acc att cac ccc agt gcc aac cgc tac ttg aca ttg gac cag gtg ttt<br>Thr Ile His Pro Ser Ala Asn Arg Tyr Leu Thr Leu Asp Gln Val Phe<br>310                     315                   320 | 1255 |
| aag cca ctg gac cca ggg tct cca caa ttg ccc gag cac ttg gaa tca<br>Lys Pro Leu Asp Pro Gly Ser Pro Gln Leu Pro Glu His Leu Glu Ser<br>325               330                   335                   340 | 1303 |
| cag cag aaa cga ccg aat cca gag ctc cgc cgg aac atg acc atc aaa<br>Gln Gln Lys Arg Pro Asn Pro Glu Leu Arg Arg Asn Met Thr Ile Lys<br>345                     350                   355 | 1351 |
| acc gaa ctc ccc ctg ggc gca cgg cgg aag atg aag cca cta cca<br>Thr Glu Leu Pro Leu Gly Ala Arg Arg Lys Met Lys Pro Leu Leu Pro<br>360                     365                   370 | 1399 |
| cgg gtc agc tca tac ctg gta cct atc cag ttc ccg gtg aac cag tca<br>Arg Val Ser Ser Tyr Leu Val Pro Ile Gln Phe Pro Val Asn Gln Ser<br>375                     380                   385 | 1447 |
| ctg gtg ttg cag ccc tcg gtg aag gtg cca ttg ccc ctg gcg gct tcc<br>Leu Val Leu Gln Pro Ser Val Lys Val Pro Leu Pro Leu Ala Ala Ser<br>390                     395                   400 | 1495 |
| ctc atg agc tca gag ctt gcc cgc cat agc aag cga gtc cgc att gcc<br>Leu Met Ser Ser Glu Leu Ala Arg His Ser Lys Arg Val Arg Ile Ala<br>405               410                   415                   420 | 1543 |
| ccc aag gtg ctg cta gct gag gag ggg ata gct cct ctt tct tct gca<br>Pro Lys Val Leu Leu Ala Glu Glu Gly Ile Ala Pro Leu Ser Ser Ala<br>425                     430                   435 | 1591 |
| gga cca ggg aaa gag gag aaa ctc ctg ttt gga gaa ggg ttt tct cct<br>Gly Pro Gly Lys Glu Glu Lys Leu Leu Phe Gly Glu Gly Phe Ser Pro<br>440                     445                   450 | 1639 |
| ttg ctt cca gtt cag act atc aag gag gaa gaa atc cag cct ggg gag<br>Leu Leu Pro Val Gln Thr Ile Lys Glu Glu Glu Ile Gln Pro Gly Glu<br>455                     460                   465 | 1687 |
| gaa atg cca cac tta gcg aga ccc atc aaa gtg gag agc cct ccc ttg<br>Glu Met Pro His Leu Ala Arg Pro Ile Lys Val Glu Ser Pro Pro Leu<br>470                     475                   480 | 1735 |
| gaa gag tgg ccc tcc ccg gcc cca tct ttc aaa gag gaa tca tct cac<br>Glu Glu Trp Pro Ser Pro Ala Pro Ser Phe Lys Glu Glu Ser Ser His<br>485               490                   495                   500 | 1783 |
| tcc tgg gag gat tcg tcc caa tct ccc acc cca aga ccc aag aag tcc<br>Ser Trp Glu Asp Ser Ser Gln Ser Pro Thr Pro Arg Pro Lys Lys Ser<br>505                     510                   515 | 1831 |

| | | | | | | | | | | | | | | | | |
|---|---|---|---|---|---|---|---|---|---|---|---|---|---|---|---|---|
| tac | agt | ggg | ctt | agg | tcc | cca | acc | cgg | tgt | gtc | tcg | gaa | atg | ctt | gtg | 1879 |
| Tyr | Ser | Gly | Leu | Arg | Ser | Pro | Thr | Arg | Cys | Val | Ser | Glu | Met | Leu | Val | |
| | | | 520 | | | | | 525 | | | | | 530 | | | |
| att | caa | cac | agg | gag | agg | agg | gag | agg | agc | cgg | tct | cgg | agg | aaa | cag | 1927 |
| Ile | Gln | His | Arg | Glu | Arg | Arg | Glu | Arg | Ser | Arg | Ser | Arg | Arg | Lys | Gln | |
| | | 535 | | | | | 540 | | | | | 545 | | | | |
| cat | cta | ctg | cct | ccc | tgt | gtg | gat | gag | ccg | gag | ctc | ctc | ttc | tca | gag | 1975 |
| His | Leu | Leu | Pro | Pro | Cys | Val | Asp | Glu | Pro | Glu | Leu | Leu | Phe | Ser | Glu | |
| | 550 | | | | | 555 | | | | | 560 | | | | | |
| ggg | ccc | agt | act | tcc | cgc | tgg | gcc | gca | gag | ctc | ccg | ttc | cca | gca | gac | 2023 |
| Gly | Pro | Ser | Thr | Ser | Arg | Trp | Ala | Ala | Glu | Leu | Pro | Phe | Pro | Ala | Asp | |
| 565 | | | | 570 | | | | | 575 | | | | | 580 | | |
| tcc | tct | gac | cct | gcc | tcc | cag | ctc | agc | tac | tcc | cag | gaa | gtg | gga | gga | 2071 |
| Ser | Ser | Asp | Pro | Ala | Ser | Gln | Leu | Ser | Tyr | Ser | Gln | Glu | Val | Gly | Gly | |
| | | | | 585 | | | | | 590 | | | | | 595 | | |
| cct | ttt | aag | aca | ccc | att | aag | gaa | acg | ctg | ccc | atc | tcc | tcc | acc | ccg | 2119 |
| Pro | Phe | Lys | Thr | Pro | Ile | Lys | Glu | Thr | Leu | Pro | Ile | Ser | Ser | Thr | Pro | |
| | | | 600 | | | | | 605 | | | | | 610 | | | |
| agc | aaa | tct | gtc | ctc | ccc | aga | acc | cct | gaa | tcc | tgg | agg | ctc | acg | ccc | 2167 |
| Ser | Lys | Ser | Val | Leu | Pro | Arg | Thr | Pro | Glu | Ser | Trp | Arg | Leu | Thr | Pro | |
| | | 615 | | | | | 620 | | | | | 625 | | | | |
| cca | gcc | aaa | gta | ggg | gga | ctg | gat | ttc | agc | cca | gta | caa | acc | tcc | cag | 2215 |
| Pro | Ala | Lys | Val | Gly | Gly | Leu | Asp | Phe | Ser | Pro | Val | Gln | Thr | Ser | Gln | |
| | 630 | | | | | 635 | | | | | 640 | | | | | |
| ggt | gcc | tct | gac | ccc | ttg | cct | gac | ccc | ctg | ggg | ctg | atg | gat | ctc | agc | 2263 |
| Gly | Ala | Ser | Asp | Pro | Leu | Pro | Asp | Pro | Leu | Gly | Leu | Met | Asp | Leu | Ser | |
| 645 | | | | 650 | | | | | 655 | | | | | 660 | | |
| acc | act | ccc | ttg | caa | agt | gct | ccc | ccc | ctt | gaa | tca | ccg | caa | agg | ctc | 2311 |
| Thr | Thr | Pro | Leu | Gln | Ser | Ala | Pro | Pro | Leu | Glu | Ser | Pro | Gln | Arg | Leu | |
| | | | | 665 | | | | | 670 | | | | | 675 | | |
| ctc | agt | tca | gaa | ccc | tta | gac | ctc | atc | tcc | gtc | ccc | ttt | ggc | aac | tct | 2359 |
| Leu | Ser | Ser | Glu | Pro | Leu | Asp | Leu | Ile | Ser | Val | Pro | Phe | Gly | Asn | Ser | |
| | | | 680 | | | | | 685 | | | | | 690 | | | |
| tct | ccc | tca | gat | ata | gac | gtc | ccc | aag | cca | ggc | tcc | ccg | gag | cca | cag | 2407 |
| Ser | Pro | Ser | Asp | Ile | Asp | Val | Pro | Lys | Pro | Gly | Ser | Pro | Glu | Pro | Gln | |
| | | 695 | | | | | 700 | | | | | 705 | | | | |
| gtt | tct | ggc | ctt | gca | gcc | aat | cgt | tct | ctg | aca | gaa | ggc | ctg | gtc | ctg | 2455 |
| Val | Ser | Gly | Leu | Ala | Ala | Asn | Arg | Ser | Leu | Thr | Glu | Gly | Leu | Val | Leu | |
| | 710 | | | | | 715 | | | | | 720 | | | | | |
| gac | aca | atg | aat | gac | agc | ctc | agc | aag | atc | ctg | ctg | gac | atc | agc | ttt | 2503 |
| Asp | Thr | Met | Asn | Asp | Ser | Leu | Ser | Lys | Ile | Leu | Leu | Asp | Ile | Ser | Phe | |
| 725 | | | | 730 | | | | | 735 | | | | | 740 | | |
| cct | ggc | ctg | gac | gag | gac | cca | ctg | ggc | cct | gac | aac | atc | aac | tgg | tcc | 2551 |
| Pro | Gly | Leu | Asp | Glu | Asp | Pro | Leu | Gly | Pro | Asp | Asn | Ile | Asn | Trp | Ser | |
| | | | | 745 | | | | | 750 | | | | | 755 | | |
| cag | ttt | att | cct | gag | cta | cag | tag | agccctgccc | ttgcccctgt | gctcaagctg | | | | | | 2605 |
| Gln | Phe | Ile | Pro | Glu | Leu | Gln | | | | | | | | | | |
| | | | 760 | | | | | | | | | | | | | |

| | |
|---|---|
| tccaccatcc cgggcactcc aaggctcagt gcacccaag cctctgagtg aggacagcag | 2665 |
| gcagggactg ttctgctcct catagctccc tgctgcctga ttatgcaaaa gtagcagtca | 2725 |
| caccctagcc actgctggga ccttgtgttc cccaagagta tctgattcct ctgctgtccc | 2785 |
| tgccaggagc tgaagggtgg gaacaacaaa ggcaatggtg aaaagagatt aggaaccccc | 2845 |
| cagcctgttt ccattctctg cccagcagtc tcttaccttc cctgatcttt gcagggtggt | 2905 |
| ccgtgtaaat agtataaatt ctccaaatta tcctctaatt ataaatgtaa gcttatttcc | 2965 |
| ttagatcatt atccagagac tgccagaagg tgggtaggat gacctggggt ttcaattgac | 3025 |

```
ttctgttcct tgcttttagt tttgatagaa gggaagacct gcagtgcacg gtttcttcca    3085
ggctgaggta cctggatctt gggttcttca ctgcagggac ccagacaagt ggatctgctt    3145
gccagagtcc ttttgcccc tccctgccac ctccccgtgt tccaagtca gctttcctgc      3205 aagaagaaat cctggttaaa aaagtctttt gtattgggtc aggagttgaa tttggggtgg    3265
gaggatggat gcaactgaag cagagtgtgg gtgcccagat gtgcgctatt agatgttct    3325 ctgataatgt ccccaatcat accagggaga ctggcattga cgagaactca ggtgaggct    3385 tgagaaggcc gaagggccc ctgacctgcc tggcttcctt agcttgcccc tcagctttgc    3445
aaagagccac cctaggcccc agctgaccgc atgggtgtga ccagcttga aacactaac    3505 tactcaataa aagcgaaggt ggacatgaaa aaaaaaaaa aaaaaa                     3551
```

<210> SEQ ID NO 9
<211> LENGTH: 763
<212> TYPE: PRT
<213> ORGANISM: Homo sapiens

<400> SEQUENCE: 9

```
Met Lys Thr Ser Pro Arg Arg Pro Leu Ile Leu Lys Arg Arg Leu
1               5                   10                  15

Pro Leu Pro Val Gln Asn Ala Pro Ser Glu Thr Ser Glu Glu Pro
                20                  25                  30

Lys Arg Ser Pro Ala Gln Gln Glu Ser Asn Gln Ala Glu Ala Ser Lys
                35                  40                  45

Glu Val Ala Glu Ser Asn Ser Cys Lys Phe Pro Ala Gly Ile Lys Ile
    50                  55                  60

Ile Asn His Pro Thr Met Pro Asn Thr Gln Val Val Ala Ile Pro Asn
65                  70                  75                  80

Asn Ala Asn Ile His Ser Ile Ile Thr Ala Leu Thr Ala Lys Gly Lys
                85                  90                  95

Glu Ser Gly Ser Ser Gly Pro Asn Lys Phe Ile Leu Ile Ser Cys Gly
                100                 105                 110

Gly Ala Pro Thr Gln Pro Pro Gly Leu Arg Pro Gln Thr Gln Thr Ser
            115                 120                 125

Tyr Asp Ala Lys Arg Thr Glu Val Thr Leu Glu Thr Leu Gly Pro Lys
    130                 135                 140

Pro Ala Ala Arg Asp Val Asn Leu Pro Arg Pro Pro Gly Ala Leu Cys
145                 150                 155                 160

Glu Gln Lys Arg Glu Thr Cys Ala Asp Gly Glu Ala Ala Gly Cys Thr
                165                 170                 175

Ile Asn Asn Ser Leu Ser Asn Ile Gln Trp Leu Arg Lys Met Ser Ser
            180                 185                 190

Asp Gly Leu Gly Ser Arg Ser Ile Lys Gln Glu Met Glu Glu Lys Glu
        195                 200                 205

Asn Cys His Leu Glu Gln Arg Gln Val Lys Val Glu Glu Pro Ser Arg
    210                 215                 220

Pro Ser Ala Ser Trp Gln Asn Ser Val Ser Glu Arg Pro Pro Tyr Ser
225                 230                 235                 240

Tyr Met Ala Met Ile Gln Phe Ala Ile Asn Ser Thr Glu Arg Lys Arg
                245                 250                 255

Met Thr Leu Lys Asp Ile Tyr Thr Trp Ile Glu Asp His Phe Pro Tyr
            260                 265                 270

Phe Lys His Ile Ala Lys Pro Gly Trp Lys Asn Ser Ile Arg His Asn
        275                 280                 285
```

-continued

Leu Ser Leu His Asp Met Phe Val Arg Glu Thr Ser Ala Asn Gly Lys
    290                 295                 300

Val Ser Phe Trp Thr Ile His Pro Ser Ala Asn Arg Tyr Leu Thr Leu
305                 310                 315                 320

Asp Gln Val Phe Lys Pro Leu Asp Pro Gly Ser Pro Gln Leu Pro Glu
                325                 330                 335

His Leu Glu Ser Gln Gln Lys Arg Pro Asn Pro Glu Leu Arg Arg Asn
            340                 345                 350

Met Thr Ile Lys Thr Glu Leu Pro Leu Gly Ala Arg Arg Lys Met Lys
        355                 360                 365

Pro Leu Pro Arg Val Ser Ser Tyr Leu Val Pro Ile Gln Phe Pro
370                 375                 380

Val Asn Gln Ser Leu Val Leu Gln Pro Ser Val Lys Val Pro Leu Pro
385                 390                 395                 400

Leu Ala Ala Ser Leu Met Ser Ser Glu Leu Ala Arg His Ser Lys Arg
                405                 410                 415

Val Arg Ile Ala Pro Lys Val Leu Leu Ala Glu Gly Ile Ala Pro
            420                 425                 430

Leu Ser Ser Ala Gly Pro Gly Lys Glu Glu Lys Leu Leu Phe Gly Glu
        435                 440                 445

Gly Phe Ser Pro Leu Leu Pro Val Gln Thr Ile Lys Glu Glu Ile
450                 455                 460

Gln Pro Gly Glu Glu Met Pro His Leu Ala Arg Pro Ile Lys Val Glu
465                 470                 475                 480

Ser Pro Pro Leu Glu Glu Trp Pro Ser Pro Ala Pro Ser Phe Lys Glu
                485                 490                 495

Glu Ser His Ser Trp Glu Asp Ser Ser Gln Ser Pro Thr Pro Arg
            500                 505                 510

Pro Lys Lys Ser Tyr Ser Gly Leu Arg Ser Pro Thr Arg Cys Val Ser
        515                 520                 525

Glu Met Leu Val Ile Gln His Arg Glu Arg Arg Glu Arg Ser Arg Ser
530                 535                 540

Arg Arg Lys Gln His Leu Leu Pro Pro Cys Val Asp Glu Pro Glu Leu
545                 550                 555                 560

Leu Phe Ser Glu Gly Pro Ser Thr Ser Arg Trp Ala Ala Glu Leu Pro
                565                 570                 575

Phe Pro Ala Asp Ser Ser Asp Pro Ala Ser Gln Leu Ser Tyr Ser Gln
            580                 585                 590

Glu Val Gly Gly Pro Phe Lys Thr Pro Ile Lys Glu Thr Leu Pro Ile
        595                 600                 605

Ser Ser Thr Pro Ser Lys Ser Val Leu Pro Arg Thr Pro Glu Ser Trp
610                 615                 620

Arg Leu Thr Pro Pro Ala Lys Val Gly Gly Leu Asp Phe Ser Pro Val
625                 630                 635                 640

Gln Thr Ser Gln Gly Ala Ser Asp Pro Leu Pro Asp Pro Leu Gly Leu
                645                 650                 655

Met Asp Leu Ser Thr Thr Pro Leu Gln Ser Ala Pro Pro Leu Glu Ser
            660                 665                 670

Pro Gln Arg Leu Leu Ser Ser Glu Pro Leu Asp Leu Ile Ser Val Pro
        675                 680                 685

Phe Gly Asn Ser Ser Pro Ser Asp Ile Asp Val Pro Lys Pro Gly Ser
690                 695                 700

```
Pro Glu Pro Gln Val Ser Gly Leu Ala Ala Asn Arg Ser Leu Thr Glu
705             710                 715                 720

Gly Leu Val Leu Asp Thr Met Asn Asp Ser Leu Ser Lys Ile Leu Leu
            725                 730                 735

Asp Ile Ser Phe Pro Gly Leu Asp Glu Asp Pro Leu Gly Pro Asp Asn
            740                 745                 750

Ile Asn Trp Ser Gln Phe Ile Pro Glu Leu Gln
            755                 760
```